United States Patent [19]

Tobin et al.

[11] Patent Number: 5,705,626
[45] Date of Patent: Jan. 6, 1998

[54] CLONED GLUTAMIC ACID DECARBOXYLASE NUCLEIC ACIDS

[75] Inventors: Allan J. Tobin, Los Angeles; Mark G. Erlander, Tarzana; Daniel L. Kaufman, Santa Monica, all of Calif.

[73] Assignee: The Regents of the University of California, Oakland, Calif.

[21] Appl. No.: 485,718

[22] Filed: Jun. 7, 1995

Related U.S. Application Data

[62] Division of Ser. No. 135,849, Oct. 13, 1993, Pat. No. 5,475,086, which is a continuation of Ser. No. 716,909, Jun. 18, 1991, abandoned, which is a continuation-in-part of Ser. No. 586,536, Sep. 21, 1990.

[51] Int. Cl.$^6$ .................... C12N 15/12; C12N 15/60
[52] U.S. Cl. ................ 536/23.5; 536/23.2; 435/232
[58] Field of Search ................ 536/23.5, 23.2; 435/232

[56] References Cited

PUBLICATIONS

Gerling et al., Effect of Coxsackie virus B4 infection in mice on expression of 64,000–Mr Autoantigen . . . , pp. 1419–1425, Oct. 1988.

Dryberg, T. Molecular Mimicry and Diabetes, pp. 117–125, 1989.

Schwimmbeck et al., Molecular Mimicry and Myashenia Gravis, pp. 1174–1180, Oct. 1989.

Todd, et al., A molecular basis for genetic susceptibility to insulin–dependent diabetes . . . , pp. 129–134 May 1988.

Wraith et al., Antigen recognition in autoimmune encephalomyelitis . . . , pp. 247–255, Oct. 1989.

Chang et al., J. Neurosci., 8(6):2123–2130, Jun. 1988.

Julien et al., J. Neurochem., 54(2):703–705, 1990.

Julien et al., Neurosci. Lett., vol. 73, pp. 173–180, 1987.

Baekkeskov et al., Diabetes, vol. 38, pp. 1133–1141, Sep. 1989.

Legay et al., J. Neurochem., 48(4): 1022–1026, 1987.

Geysen et al., PNAS, vol. 81, pp. 3998–4002, Jul. 1984.

*Primary Examiner*—Keith D. Hendricks
*Attorney, Agent, or Firm*—Bertram I. Rowland

[57] ABSTRACT

The invention is directed to isolated polypeptides useful in ameliorating autoimmune disease.

6 Claims, 9 Drawing Sheets

```
GGGCGTGCGGGGTCGAGCCGAAGCAGCTTGCCCGCAGCCACTCGGAGGCGACCAGCGCCA
        10                  30                  50
                        M  A  S  P  G  S  G  F  W  S  F  G  S  E  D  G
GACTAGCAGAACCCATGGCATCTCCGGCTCTGGCTTTTGGTCCTTCGGATCTGAAGATG
        70                  90                 110
  S  G  D  P  E  N  P  G  T  A  R  A  W  C  Q  V  A  Q  K  F
GCTCTGGGGATCCTGAGAACCCGGGAACAGCGAGAGCCTGGTGCCAGGTGGCCCAAAAGT
       130                 150                 170
    T  G  G  I  G  N  K  L  C  A  L  L  Y  G  D  S  E  K  P  A
TCACGGGCGGCATCGGAAACAAGCTATGCGCTCTGCTCTACGGAGACTCTGAGAAGCCAG
       190                 210                 230
  E  S  G  G  S  V  T  S  R  A  A  T  R  K  V  A  C  T  C  D
CAGAGAGCGGCGGGAGCGTGACCTCGCGGGCCGCCACTCGGAAGGTCGCCTGCACCTGTG
       250                 270                 290
  Q  K  P  C  S  C  P  K  G  D  V  N  Y  A  L  L  H  A  T  D
ACCAAAAACCCTGCAGCTGCCCCAAAGGAGATGTCAATTATGCACTTCTCCACGCAACAG
       310                 330                 350
  L  L  P  A  C  E  G  E  R  P  T  L  A  F  L  Q  D  V  M  N
ACCTGCTGCCAGCCTGTGAAGGAGAAAGGCCCACTCTCGCATTTCTGCAAGATGTAATGA
       370                 390                 410
  I  L  L  Q  Y  V  V  K  S  F  D  R  S  T  K  V  I  D  F  H
ACATTTTGCTTCAGTACGTGGTGAAAAGTTTTGATAGATCAACTAAAGTGATTGATTTCC
       430                 450                 470
  Y  P  N  E  L  L  Q  E  Y  N  W  E  L  A  D  Q  P  Q  N  L
ATTACCCCAATGAGCTTCTTCAAGAGTATAATTGGGAATTGGCAGACCAACCGCAAAATC
       490                 510                 530
  E  E  I  L  T  H  C  Q  T  T  L  K  Y  A  I  K  T  G  H  P
TGGAGGAAATTTTGACGCACTGCCAAACAACTCTAAAATATGCGATTAAAACAGGGCATC
       550                 570                 590
  R  Y  F  N  Q  L  S  T  G  L  D  M  V  G  L  A  A  D  W  L
CCCGATATTTTAATCAGCTGTCTACCGGATTGGATATGGTTGGATTAGCAGCAGATTGGT
       610                 630                 650
  T  S  T  A  N  T  N  M  F  T  Y  E  I  A  P  V  F  V  L  L
TGACATCAACAGCAAACACGAACATGTTTACCTATGAGATCGCCCCTGTATTTGTACTAC
       670                 690                 710
  E  Y  V  T  L  K  K  M  R  E  I  I  G  W  P  G  G  S  G  D
TGGAATATGTGACACTAAAGAAAATGAGGGAAATCATTGGCTGGCCAGGAGGCTCTGGCG
       730                 750                 770
  G  I  F  S  P  G  G  A  I  S  N  M  Y  A  M  L  I  A  R  Y
ATGGAATCTTTTCTCCTGGTGGTGCCATCTCCAACATGTACGCCATGCTCATTGCCCGCT
       790                 810                 830
  K  M  F  P  E  V  K  E  K  G  M  A  A  V  P  R  L  I  A  F
ATAAGATGTTTCCAGAAGTCAAGGAAAAGGGGATGGCGGCGGTGCCCAGGCTCATCGCAT
       850                 870                 890
  T  S  E  H  S  H  F  S  L  K  K  G  A  A  A  L  G  I  G  T
TCACGTCAGAGCATAGTCACTTTTCTCTCAAGAAGGGAGCTGCAGCCTTGGGGATCGGAA
       910                 930                 950
  D  S  V  I  L  I  K  C  D  E  R  G  K  M  I  P  S  D  L  E
CAGACAGCGTGATTCTGATTAAATGTGATGAGAGAGGGAAAATGATCCCATCTGACCTTG
       970                 990                1010
  R  R  I  L  E  V  K  Q  K  G  F  V  P  F  L  V  S  A  T  A
AAAGAAGAATCCTTGAAGTCAAACAGAAAGGATTTGTTCCTTTCCTGGTGAGTGCCACAG
      1030                1050                1070
  G  T  T  V  Y  G  A  F  D  P  L  L  A  V  A  D  I  C  K  K
CTGGAACCACTGTGTACGGGGCTTTTGATCCTCTCTTGGCTGTAGCTGACATCTGCAAAA
      1090                1110                1130
  Y  K  I  W  M  H  V  D  A  A  W  G  G  G  L  L  M  S  R  K
AATATAAGATCTGGATGCATGTGGATGCTGCTTGGGGTGGAGGGTTACTGATGTCTCGGA
      1150                1170                1190
  H  K  W  K  L  N  G  V  E  R  A  N  S  V  T  W  N  P  H  K
AACACAAGTGGAAGCTGAACGGTGTGGAGAGGGCCAACTCTGTGACATGGAATCCCCACA
      1210                1230                1250
  M  M  G  V  P  L  Q  C  S  A  L  L  V  R  E  E  G  L  M  Q
AGATGATGGGTGTCCCCTTGCAATGTTCGGCTCTCCTGGTCAGAGAGGAGGGACTGATGC
```

FIG.2A

```
      1270                    1290                    1310
   S   C   N   Q   M   H   A   S   Y   L   F   Q   Q   D   K   H   Y   D   L   S
AGAGCTGCAACCAGATGCATGCTTCCTACCTCTTTCAGCAAGATAAGCACTATGACCTGT
      1330                    1350                    1370
   Y   D   T   G   D   K   A   L   Q   C   G   R   H   V   D   V   F   K   L   W
CCTATGACACGGGAGACAAGGCCTTGCAGTGTGGACGCCACGTCGATGTCTTTAAATTAT
      1390                    1410                    1430
   L   M   W   R   A   K   G   T   T   G   F   E   A   H   I   D   K   C   L   E
GGCTCATGTGGAGAGCAAAGGGGACTACTGGATTTGAAGCTCACATTGATAAGTGTTTGG
      1450                    1470                    1490
   L   A   E   Y   L   Y   N   I   I   K   N   R   E   G   Y   E   M   V   F   D
AGCTGGCAGAGTATTTATACAATATCATTAAAAACCGAGAAGGATATGAAATGGTGTTCG
      1510                    1530                    1550
   G   K   P   Q   H   T   N   V   C   F   W   F   V   P   P   S   L   R   V   L
ATGGGAAGCCTCAGCACACAAATGTCTGCTTCTGGTTTGTACCTCCTAGTTTGCGAGTTC
      1570                    1590                    1610
   E   D   N   E   E   R   M   S   R   L   S   K   V   A   P   V   I   K   A   R
TGGAAGACAATGAAGAGAGAATGAGCCGCCTCTCAAAGGTGGCGCCAGTGATTAAAGCCA
      1630                    1650                    1670
   M   M   E   Y   G   T   T   M   V   S   Y   Q   P   L   G   D   K   V   N   F
GAATGATGGAGTATGGGACCACAATGGTCAGCTACCAACCCTTAGGAGATAAGGTCAACT
      1690                    1710                    1730
   F   R   M   V   I   S   N   P   A   A   T   H   Q   D   I   D   F   L   I   E
TCTTCCGCATGGTCATCTCAAACCCTGCAGCAACTCACCAAGACATTGACTTCCTCATTG
      1750                    1770                    1790
   E   I   E   R   L   G   Q   D   L   *
AAGAAATCGAACGCCTGGGACAAGATTTGTAATCACTTTGCTCACCAAACTTTCAGTTCT
      1810                    1830                    1850
CTAGGTAGACAGCTAAGTTGTCACAAACTGTGTAAATGTATTTGTAGTTTGTTCCAGAGT
      1870                    1890                    1910
AATTCTATTTCTATATCGTGGTGTCACAGTAGAGTCCAGTTTAAAA
      1930                    1950
```

FIG.2B

```
                                                                          M   A   S
AGCTCGCCCGCAGCTCGCACTCGCAGGCGACCTGCTCCAGTCTCCAAAGCCGATGGCATC
          10                      30                      50
  P   G   S   G   F   W   S   F   G   S   E   D   G   S   G   D   S   E   N   P
TCCGGGCTCTGGCTTTTGGTCTTTCGGGTCGGAAGATGGCTCTGGGGATTCCGAGAATCC
          70                      90                     110
  G   T   A   R   A   W   C   Q   V   A   Q   K   F   T   G   G   I   G   N   K
CGGCACAGCGCGAGCCTGGTGCCAAGTGGCTCAGAAGTTCACGGGCGGCATCGGAAACAA
         130                     150                     170
  L   C   A   L   L   Y   G   D   A   E   K   P   A   E   S   G   G   S   Q   P
ACTGTGCGCCCTGCTCTACGGAGACGCCGAGAAGCCGGCGGAGAGCGGCGGGAGCCAACC
         190                     210                     230
  P   R   A   A   A   R   K   A   A   C   A   C   D   Q   K   P   C   S   C   S
CCCGCGGGCCGCCGCCCGGAAGGCCGCCTGCGCCTGCGACCAGAAGCCCTGCAGCTGCTC
         250                     270                     290
  K   V   D   V   N   Y   A   F   L   H   A   T   D   L   L   P   A   C   D   G
CAAAGTGGATGTCAACTACGCGTTTCTCCATGCAACAGACCTGCTGCCGGCGTGTGATGG
         310                     330                     350
  E   R   P   T   L   A   F   L   Q   D   V   M   N   I   L   L   Q   Y   V   V
AGAAAGGCCCACTTTGGCGTTTCTGCAAGATGTTATGAACATTTTACTTCAGTATGTGGT
         370                     390                     410
  K   S   F   D   R   S   T   K   V   I   D   F   H   Y   P   N   E   L   L   Q
GAAAAGTTTCGATAGATCAACCAAAGTGATTGATTTCCATTATCCTAATGAGCTTCTCCA
         430                     450                     470
  E   Y   N   W   E   L   A   D   Q   P   Q   N   L   E   E   I   L   M   H   C
AGAATATAATTGGGAATTGGCAGACCAACCACAAAATTTGGAGGAAATTTTGATGCATTG
         490                     510                     530
  Q   T   T   L   K   Y   A   I   K   T   G   H   P   R   Y   F   N   Q   L   S
CCAAACAACTCTAAAATATGCAATTAAAACAGGGCATCCTAGATACTTCAATCAACTTTC
         550                     570                     590
  T   G   L   D   M   V   G   L   A   A   D   W   L   T   S   T   A   N   T   N
TACTGGTTTGGATATGGTTGGATTAGCAGCAGACTGGCTGACATCAACAGCAAATACTAA
         610                     630                     650
  M   F   T   Y   E   I   A   P   V   F   V   L   L   E   Y   V   T   L   K   K
CATGTTCACCTATGAAATTGCTCCAGTATTTGTGCTTTTGGAATATGTCACACTAAAGAA
         670                     690                     710
  M   R   E   I   I   G   W   P   G   G   S   G   D   G   I   F   S   P   G   G
AATGAGAGAAATCATTGGCTGGCCAGGGGGCTCTGGCGATGGGATATTTTCTCCCGGTGG
         730                     750                     770
  A   I   S   N   M   Y   A   M   M   I   A   R   F   K   M   F   P   E   V   K
CGCCATATCTAACATGTATGCCATGATGATCGCACGCTTTAAGATGTTCCCAGAAGTCAA
         790                     810                     830
  E   K   G   M   A   A   L   P   R   L   I   A   F   T   S   E   H   S   H   F
GGAGAAAGGAATGGCTGCTCTTCCCAGGCTCATTGCCTTCACGTCTGAACATAGTCATTT
         850                     870                     890
  S   L   K   K   G   A   A   A   L   G   I   G   T   D   S   V   I   L   I   K
TTCTCTCAAGAAGGGAGCTGCAGCCTTAGGGATTGGAACAGACAGCGTGATTCTGATTAA
         910                     930                     950
  C   D   E   R   G   K   M   I   P   S   D   L   E   R   R   I   L   E   A   K
ATGTGATGAGAGAGGGAAAATGATTCCATCTGATCTTGAAAGAAGGATTCTTGAAGCCAA
         970                     990                    1010
  Q   K   G   F   V   P   F   L   V   S   A   T   A   G   T   T   V   Y   G   A
ACAGAAAGGGTTTGTTCCTTTCCTCGTGAGTGCCACAGCTGGAACCACCGTGTACGGAGC
        1030                    1050                    1070
  F   D   P   L   L   A   V   A   D   I   C   K   K   Y   K   I   W   M   H   V
ATTTGACCCCCTCTTAGCTGTCGCTGACATTTGCAAAAAGTATAAGATCTGGATGCATGT
        1090                    1110                    1130
```

FIG.3A

```
        D   A   A   W   G   G   G   L   L   M   S   R   K   H   K   W   K   L   S   G
       GGATGCAGCTTGGGGTGGGGGATTACTGATGTCCCGAAAACACAAGTGGAAACTGAGTGG
              1150                1170                1190
        V   E   R   A   N   S   V   T   W   N   P   H   K   M   M   G   V   P   L   Q
       CGTGGAGAGGGCCAACTCTGTGACGTGGAATCCACACAAGATGATGGGAGTCCCTTTGCA
              1210                1230                1250
        C   S   A   L   L   V   R   E   E   G   L   M   Q   N   C   N   Q   M   H   A
       GTGCTCTGCTCTCCTGGTTAGAGAAGAGGGATTGATGCAGAATTGCAACCAAATGCATGC
              1270                1290                1310
        S   Y   L   F   Q   Q   D   K   H   Y   D   L   S   Y   D   T   G   D   K   A
       CTCCTACCTCTTTCAGCAAGATAAACATTATGACCTGTCCTATGACACTGGAGACAAGGC
              1330                1350                1370
        L   Q   C   G   R   H   V   D   V   F   K   L   W   L   M   W   R   A   K   G
       CTTACAGTGCGGACGCCACGTTGATGTTTTTAAACTATGGCTGATGTGGAGGGCAAAGGG
              1390                1410                1430
        T   T   G   F   E   A   H   V   D   K   C   L   E   L   A   E   Y   L   Y   N
       GACTACCGGGTTTGAAGCGCATGTTGATAAATGTTTGGAGTTGGCAGAGTATTTATACAA
              1450                1470                1490
        I   I   K   N   R   E   G   Y   E   M   V   F   D   G   K   P   Q   H   T   N
       CATCATAAAAAACCGAGAAGGATATGAGATGGTGTTTGATGGGAAGCCTCAGCACACAAA
              1510                1530                1550
        V   C   F   W   Y   I   P   P   S   L   R   T   L   E   D   N   E   E   R   M
       TGTCTGCTTCTGGTACATTCCTCCAAGCTTGCGTACTCTGGAAGACAATGAAGAGAGAAT
              1570                1590                1610
        S   R   L   S   K   V   A   P   V   I   K   A   R   M   M   E   Y   G   T   T
       GAGTCGCCTCTCGAAGGTGGCTCCAGTGATTAAAGCCAGAATGATGGAGTATGGAACCAC
              1630                1650                1670
        M   V   S   Y   Q   P   L   G   D   K   V   N   F   F   R   M   V   I   S   N
       AATGGTCAGCTACCAACCCTTGGGAGACAAGGTCAATTTCTTCCGCATGGTCATCTCAAA
              1690                1710                1730
        P   A   A   T   H   Q   D   I   D   F   L   I   E   E   I   E   R   L   G   Q
       CCCAGCGGCAACTCACCAAGACATTGACTTCCTGATTGAAGAAATAGAACGCCTTGGACA
              1750                1770                1790
        D   L   *
       AGATTTATAATAACCTTGCTCACCAAGCTGTTCCACTTCTCTAGGTAGACAATTAAGTTG
              1810                1830                1850
       TCACAAACTGTGTGAATGTATTTGTAGTTTGTTCCAAAGTAAATCTATTTCTATATTGTG
              1870                1890                1910
       GTGTCAAAGTAGAGTTTAAAAATTAAACAAAAAAGACATTGCTCCTTTTAAAAGTCCTTT
              1930                1950                1970
       CTTAAGTTTAGAATACCTCTCTAAGAATTCGTGACAAAAGGCTATGTTCTAATCAATAAG
              1990                2010                2030
       GAAAAGCTTAAAATTGTTATAAATACTTCCCTTACTTTTAATATAGTGTGCAAAGCAAAC
              2050                2070                2090
```

FIG.3B

```
            Gap Weight:    3.000      Average Match:     0.540
         Length Weight:    0.100   Average Mismatch:    -0.396

Quality:  856.2             Length:      585
                  Ratio:  1.464               Gaps:        0
     Percent Similarity: 97.436    Percent Identity:   96.068

4817.Pep x Hgt2.Pep       August 22, 1990  08:20   ..
```

```
  1 MASPGSGFWSFGSEDGSGDPENPGTARAWCQVAQKFTGGIGNKLCALLYG 50
    |||||||||||||||||||.|||||||||||||||||||||||||||||
  1 MASPGSGFWSFGSEDGSGDSENPGTARAWCQVAQKFTGGIGNKLCALLYG 50

51 DSEKPAESGGSVTSRAATRKVACTCDQKPCSCPKGDVNYALLHATDLLPA 100
    |.|||||||||..||.||||.|.|||||||||..||||||.|||||||| 
 51 DAEKPAESGGSQPPRAAARKAACACDQKPCSCSKVDVNYAFLHATDLLPA 100

101 CEGERPTLAFLQDVMNILLQYVVKSFDRSTKVIDFHYPNELLQEYNWELA 150
    |:|||||||||||||||||||||||||||||||||||||||||||||||
101 CDGERPTLAFLQDVMNILLQYVVKSFDRSTKVIDFHYPNELLQEYNWELA 150

151 DQPQNLEEILTHCQTTLKYAIKTGHPRYFNQLSTGLDMVGLAADWLTSTA 200
    |||||||||:|||||||||||||||||||||||||||||||||||||||
151 DQPQNLEEILMHCQTTLKYAIKTGHPRYFNQLSTGLDMVGLAADWLTSTA 200

201 NTNMFTYEIAPVFVLLEYVTLKKMREIIGWPGGSGDGIFSPGGAISNMYA 250
    |||||||||||||||||||||||||||||||||||||||||||||||||
201 NTNMFTYEIAPVFVLLEYVTLKKMREIIGWPGGSGDGIFSPGGAISNMYA 250

251 MLIARYKMFPEVKEKGMAAVPRLIAFTSEHSFSLKKGAAALGIGTDSVI 300
    |:|||:|||||||||||||:|||||||||||||||||||||||||||||
251 MMIARFKMFPEVKEKGMAALPRLIAFTSEHSFSLKKGAAALGIGTDSVI 300

301 LIKCDERGKMIPSDLERRILEVKQKGFVPFLVSATAGTTVYGAFDPLLAV 350
    ||||||||||||||||||||.||||||||||||||||||||||||||||
301 LIKCDERGKMIPSDLERRILEAKQKGFVPFLVSATAGTTVYGAFDPLLAV 350

351 ADICKKYKIWMHVDAAWGGGLLMSRKHKWKLNGVERANSVTWNPHKMMGV 400
    ||||||||||||||||||||||||||||||.||||||||||||||||||
351 ADICKKYKIWMHVDAAWGGGLLMSRKHKWKLSGVERANSVTWNPHKMMGV 400

401 PLQCSALLVREEGLMQSCNQMHASYLFQQDKHYDLSYDTGDKALQCGRHV 450
    |||||||||||||||.|||||||||||||||||||||||||||||||||
401 PLQCSALLVREEGLMQNCNQMHASYLFQQDKHYDLSYDTGDKALQCGRHV 450

451 DVFKLWLMWRAKGTTGFEAHIDKCLELAEYLYNIIKNREGYEMVFDGKPQ 500
    ||||||||||||||||||||:||||||||||||||||||||||||||||
451 DVFKLWLMWRAKGTTGFEAHVDKCLELAEYLYNIIKNREGYEMVFDGKPQ 500

501 HTNVCFWFVPPSLRVLEDNEERMSRLSKVAPVIKARMMEYGTTMVSYQPL 550
    ||||||::|||||.|||||||||||||||||||||||||||||||||||
501 HTNVCFWYIPPSLRTLEDNEERMSRLSKVAPVIKARMMEYGTTMVSYQPL 550

551 GDKVNFFRMVISNPAATHQDIDFLIEEIERLGQDL 585
    ||||||||||||||||||||||||||||||||||
551 GDKVNFFRMVISNPAATHQDIDFLIEEIERLGQDL 585
```

FIG.4

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Ser Ile Ala Ala Arg Tyr Lys Tyr Phe Pro Glu Val Lys Thr Lys Gly
1               5                   10                  15

Met Ala Ala Val Pro Lys Leu
                20

( 2 ) INFORMATION FOR SEQ ID NO:2:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Ala Met Met Ile Ala Arg Phe Lys Met Phe Pro Glu Val Lys Glu Lys
1               5                   10                  15

Gly Met Ala Ala Leu Pro Arg Leu
                20

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Phe Ile Glu Trp Leu Lys Val Lys Ile Leu Pro Glu Val Lys Glu Lys
1               5                   10                  15

His Glu Phe Leu Ser Arg Leu
                20

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Lys Ser Met Cys Pro Gln Ala Gln Leu Lys Val Lys Tyr Leu
 1               5                   10                  15
```

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Ala Arg Phe Lys Met Phe Pro Glu Val Lys Glu Lys Gly Met Ala Ala
 1               5                   10                  15
```

( 2 ) INFORMATION FOR SEQ ID NO:6:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Tyr Glu Ile Ala Pro Val Phe Val Leu Met Glu Gln Ile Thr Leu Lys
 1               5                   10                  15

Lys Met Arg Glu Ile Val Gly Trp Ser Ser Lys Asp Gly Asp Gly Ile
                20                  25                  30

Phe Ser Pro Gly Gly Ala Ile Ser Asn Met Tyr Ser Ile Met Ala Ala
                35                  40                  45

Arg Tyr Lys Phe Phe Pro Glu Val Lys Thr Lys Gly
 50                  55                  60
```

( 2 ) INFORMATION FOR SEQ ID NO:7:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Tyr Glu Ile Ala Pro Val Phe Val Leu Leu Glu Tyr Val Arg Glu Ile
 1               5                   10                  15

Ile Gly Trp Pro Gly Gly Ser Asp Gly Ile Phe Ser Pro Gly Gly Ala
                20                  25                  30

Ile Ser Asn Tyr Ala Met Leu Ile Ala Arg Tyr Lys Met Phe Pro Glu
                35                  40                  45

Val Lys Glu Lys Gly
 50
```

( 2 ) INFORMATION FOR SEQ ID NO:8:

( i ) SEQUENCE CHARACTERISTICS:
        ( A ) LENGTH: 2026 base pairs
        ( B ) TYPE: nucleic acid ( C ) STRANDEDNESS: single
( D ) TOPOLOGY: linear ( i i ) MOLECULE TYPE: peptide ( x i ) SEQUENCE DESCRIPTION: SEQ ID NO:8:

| | | | | | | |
|---|---|---|---|---|---|---|
| GGGCGTGCGG | GGTCGAGCCG | AAGCAGCTTG | CCCGCAGCCA | CTCGGAGGCG | ACCAGCGCCA | 60 |
| GACTAGCAGA | ACCCATGGCA | TCTCCGGGCT | CTGGCTTTTG | GTCCTTCGGA | TCTGAAGATG | 120 |
| GCTCTGGGGA | TCCTGAGAAC | CCGGGAACAG | CGAGAGCCTG | GTGCCAGGTG | GCCCAAAAGT | 180 |
| TCACGGGCGG | CATCGGAAAC | AAGCTATGCG | CTCTGCTCTA | CGGAGACTCT | GAGAAGCCAG | 240 |
| CAGAGAGCGG | CGGGAGCGTG | ACCTCGCGGG | CCGCCACTCG | GAAGGTCGCC | TGCACCTGTG | 300 |
| ACCAAAAACC | CTGCAGCTGC | CCCAAGGAG | ATGTCAATTA | TGCACTTCTC | CACGCAACAG | 360 |
| ACCTGCTGCC | AGCCTGTGAA | GGAGAAAGGC | CCACTCTCGC | ATTTCTGCAA | GATGTAATGA | 420 |
| ACATTTGCT | TCAGTACGTG | GTGAAAAGTT | TTGATAGATC | AACTAAAGTG | ATTGATTTCC | 480 |
| ATTACCCCAA | TGAGCTTCTT | CAAGAGTATA | ATTGGGAATT | GGCAGACCAA | CCGCAAAATC | 540 |
| TGGAGGAAAT | TTTGACGCAC | TGCCAAACAA | CTCTAAAATA | TGCGATTAAA | ACAGGGCATC | 600 |
| CCCGATATTT | TAATCAGCTG | TCTACCGGAT | GGATATGGT | TGGATTAGCA | GCAGATTGGT | 660 |
| TGACATCAAC | AGCAAACACG | AACATGTTTA | CCTATGAGAT | CGCCCCTGTA | TTTGTACTAC | 720 |
| TGGAATATGT | GACACTAAAG | AAAATGAGGG | AAATCATTGG | CTGGCCAGGA | GGCTCTGGCG | 780 |
| ATGGAATCTT | TTCTCCTGGT | GGTGCCATCT | CCAACATGTA | CGCCATGCTC | ATTGCCCGCT | 840 |
| ATAAGATGTT | TCCAGAAGTC | AAGGAAAAGG | GGATGGCGGC | GGTGCCCAGG | CTCATCGCAT | 900 |
| TCACGTCAGA | GCATAGTCAC | TTTTCTCTCA | AGAAGGGAGC | TGCAGCCTTG | GGGATCGGAA | 960 |
| CAGACAGCGT | GATTCTGATT | AAATGTGATG | AGAGAGGGAA | AATGATCCCA | TCTGACCTTG | 1020 |
| AAGAAGAAT | CCTTGAAGTC | AAACAGAAAG | GATTTGTTCC | TTTCCTGGTG | AGTGCCACAG | 1080 |
| AAAGAAGAAT | CCTTGAAGTC | AAACAGAAAG | GATTTGTTCC | TTTCCTGGTG | AGTGCCACAG | 1140 |
| CTGGAACCAC | TGTGTACGGG | GCTTTTGATC | CTCTCTTGGC | TGTAGCTGAC | ATCTGCAAAA | 1200 |
| AATATAAGAT | CTGGATGCAT | GTGGATGCTG | CTTGGGGTGG | AGGGTTACTG | ATGTCTCGGA | 1260 |
| AACACAAGTG | GAAGCTGAAC | GGTGTGGAGA | GGGCCAACTC | TGTGACATGG | AATCCCCACA | 1320 |
| AGATGATGGG | TGTCCCCTTG | CAATGTTCGG | CTCTCCTGGT | CAGAGAGGAG | GGACTGATGC | 1380 |
| AGAGCTGCAA | CCAGATGCAT | GCTTCCTACC | TCTTTCAGCA | AGATAAGCAC | TATGACCTGT | 1440 |
| CCTATGACAC | GGGAGACAAG | GCCTTGCAGT | GTGGACGCCA | CGTCGATGTC | TTTAAATTAT | 1500 |
| GGCTCATGTG | GAGAGCAAAG | GGGACTACTG | GATTTGAAGC | TCACATTGAT | AAGTGTTTGG | 1560 |
| AGCTGGCAGA | GTATTTATAC | AATATCATTA | AAAACCGAGA | AGGATATGAA | ATGGTGTTCG | 1620 |
| ATGGGAAGCC | TCAGCACACA | AATGTCTGCT | TCTGGTTTGT | ACCTCCTAGT | TTGCGAGTTC | 1680 |
| TGGAAGACAA | TGAAGAGAGA | ATGAGCCGCC | TCTCAAAGGT | GGCGCCAGTG | ATTAAAGCCA | 1740 |
| GAATGATGGA | GTATGGGACC | ACAATGGTCA | GCTACCAACC | CTTAGGAGAT | AAGGTCAACT | 1800 |
| TCTTCCGCAT | GGTCATCTCA | AACCCTGCAG | CAACTCACCA | AGACATTGAC | TTCCTCATTG | 1860 |
| AAGAAATCGA | ACGCCTGGGA | CAAGATTTGT | AATCACTTTG | CTCACCAAAC | TTTCAGTTCT | 1920 |
| CTAGGTAGAC | AGCTAAGTTG | TCACAAACTG | TGTAAATGTA | TTTGTAGTTT | GTTCCAGAGT | 1980 |
| AATTCTATTT | CTATATCGTG | GTGTCACAGT | AGAGTCCAGT | TTAAAA | | 2026 |

( 2 ) INFORMATION FOR SEQ ID NO:9:

( i ) SEQUENCE CHARACTERISTICS:
( A ) LENGTH: 605 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

| Met | Ala | Ser | Pro | Gly | Ser | Gly | Phe | Trp | Ser | Phe | Gly | Ser | Glu | Asp | Gly |
|---|---|---|---|---|---|---|---|---|---|---|---|---|---|---|---|
| 1 | | | | 5 | | | | | 10 | | | | | 15 | |
| Ser | Gly | Asp | Pro | Glu | Asn | Pro | Gly | Thr | Ala | Arg | Ala | Trp | Cys | Gln | Val |
| | | | 20 | | | | | 25 | | | | | 30 | | |
| Ala | Gln | Lys | Phe | Thr | Gly | Gly | Ile | Gly | Asn | Lys | Leu | Cys | Ala | Leu | Leu |
| | | | 35 | | | | 40 | | | | | 45 | | | |
| Tyr | Gly | Asp | Ser | Glu | Lys | Pro | Ala | Glu | Ser | Gly | Gly | Ser | Val | Thr | Ser |
| | 50 | | | | | 55 | | | | | 60 | | | | |
| Arg | Ala | Ala | Thr | Arg | Lys | Val | Ala | Cys | Thr | Cys | Asp | Gln | Lys | Pro | Cys |
| 65 | | | | | 70 | | | | | 75 | | | | | 80 |
| Ser | Cys | Pro | Lys | Gly | Asp | Val | Asn | Tyr | Ala | Leu | Leu | His | Ala | Thr | Asp |
| | | | | 85 | | | | | 90 | | | | | 95 | |
| Leu | Leu | Pro | Ala | Cys | Glu | Gly | Glu | Arg | Pro | Thr | Leu | Ala | Phe | Leu | Gln |
| | | | 100 | | | | | 105 | | | | | 110 | | |
| Asp | Val | Met | Asn | Ile | Leu | Leu | Gln | Tyr | Val | Val | Lys | Ser | Phe | Asp | Arg |
| | | 115 | | | | | 120 | | | | | 125 | | | |
| Ser | Thr | Lys | Val | Ile | Asp | Phe | His | Tyr | Pro | Asn | Glu | Leu | Leu | Gln | Glu |
| | 130 | | | | | 135 | | | | | 140 | | | | |
| Tyr | Asn | Trp | Glu | Leu | Ala | Asp | Gln | Pro | Gln | Asn | Leu | Glu | Glu | Ile | Leu |
| 145 | | | | | 150 | | | | | 155 | | | | | 160 |
| Thr | His | Cys | Gln | Thr | Thr | Leu | Lys | Tyr | Ala | Ile | Lys | Thr | Gly | His | Pro |
| | | | | 165 | | | | | 170 | | | | | 175 | |
| Arg | Tyr | Phe | Asn | Gln | Leu | Ser | Thr | Gly | Leu | Asp | Met | Val | Gly | Leu | Ala |
| | | | 180 | | | | | 185 | | | | | 190 | | |
| Ala | Asp | Trp | Leu | Thr | Ser | Thr | Ala | Asn | Thr | Asn | Met | Phe | Thr | Tyr | Glu |
| | | 195 | | | | | 200 | | | | | 205 | | | |
| Ile | Ala | Pro | Val | Phe | Val | Leu | Leu | Glu | Tyr | Val | Thr | Leu | Lys | Lys | Met |
| | 210 | | | | | 215 | | | | | 220 | | | | |
| Arg | Glu | Ile | Ile | Gly | Trp | Pro | Gly | Gly | Ser | Gly | Asp | Gly | Ile | Phe | Ser |
| 225 | | | | | 230 | | | | | 235 | | | | | 240 |
| Pro | Gly | Gly | Ala | Ile | Ser | Asn | Met | Tyr | Ala | Met | Leu | Ile | Ala | Arg | Tyr |
| | | | | 245 | | | | | 250 | | | | | 255 | |
| Lys | Met | Phe | Pro | Glu | Val | Lys | Glu | Lys | Gly | Met | Ala | Ala | Val | Pro | Arg |
| | | | 260 | | | | | 265 | | | | | 270 | | |
| Leu | Ile | Ala | Phe | Thr | Ser | Glu | His | Ser | His | Phe | Ser | Leu | Lys | Lys | Gly |
| | | 275 | | | | | 280 | | | | | 285 | | | |
| Ala | Ala | Ala | Leu | Gly | Ile | Gly | Thr | Asp | Ser | Val | Ile | Leu | Ile | Lys | Cys |
| | 290 | | | | | 295 | | | | | 300 | | | | |
| Asp | Glu | Arg | Gly | Lys | Met | Ile | Pro | Ser | Asp | Leu | Glu | Arg | Arg | Ile | Leu |
| 305 | | | | | 310 | | | | | 315 | | | | | 320 |
| Glu | Val | Lys | Gln | Lys | Gly | Phe | Val | Pro | Phe | Leu | Val | Ser | Ala | Thr | Ala |
| | | | | 325 | | | | | 330 | | | | | 335 | |
| Arg | Arg | Ile | Leu | Glu | Val | Lys | Gln | Lys | Gly | Phe | Val | Pro | Phe | Leu | Val |
| | | | 340 | | | | | 345 | | | | | 350 | | |
| Ser | Ala | Thr | Ala | Gly | Thr | Thr | Val | Tyr | Gly | Ala | Phe | Asp | Pro | Leu | Leu |
| | | 355 | | | | | 360 | | | | | 365 | | | |
| Ala | Val | Ala | Asp | Ile | Cys | Lys | Lys | Tyr | Lys | Ile | Trp | Met | His | Val | Asp |
| | 370 | | | | | 375 | | | | | 380 | | | | |

|   |   |   |   |   |   |   |   |   |   |   |   |   |   |   |
|---|---|---|---|---|---|---|---|---|---|---|---|---|---|---|
| Ala 385 | Ala | Trp | Gly | Gly 390 | Gly | Leu | Leu | Met | Ser 395 | Arg | Lys | His | Lys | Trp | Lys 400 |
| Leu | Asn | Gly | Val | Glu 405 | Arg | Ala | Asn | Ser | Val 410 | Thr | Trp | Asn | Pro | His 415 | Lys |
| Met | Met | Gly | Val 420 | Pro | Leu | Gln | Cys | Ser 425 | Ala | Leu | Leu | Val | Arg 430 | Glu | Glu |
| Gly | Leu | Met 435 | Gln | Ser | Cys | Asn | Gln 440 | Met | His | Ala | Ser | Tyr 445 | Leu | Phe | Gln |
| Gln | Asp 450 | Lys | His | Tyr | Asp | Leu 455 | Ser | Tyr | Asp | Thr | Gly 460 | Asp | Lys | Ala | Leu |
| Gln 465 | Cys | Gly | Arg | His | Val 470 | Asp | Val | Phe | Lys | Leu 475 | Trp | Leu | Met | Trp | Arg 480 |
| Ala | Lys | Gly | Thr | Thr 485 | Gly | Phe | Glu | Ala | His 490 | Ile | Asp | Lys | Cys | Leu 495 | Glu |
| Leu | Ala | Glu | Tyr 500 | Leu | Tyr | Asn | Ile | Ile 505 | Lys | Asn | Arg | Glu | Gly 510 | Tyr | Glu |
| Met | Val | Phe 515 | Asp | Gly | Lys | Pro | Gln 520 | His | Thr | Asn | Val | Cys 525 | Phe | Trp | Phe |
| Val | Pro 530 | Pro | Ser | Leu | Arg | Val 535 | Leu | Glu | Asp | Asn | Glu 540 | Glu | Arg | Met | Ser |
| Arg 545 | Leu | Ser | Lys | Val | Ala 550 | Pro | Val | Ile | Lys | Ala 555 | Arg | Met | Met | Glu | Tyr 560 |
| Gly | Thr | Thr | Met | Val 565 | Ser | Tyr | Gln | Pro | Leu 570 | Gly | Asp | Lys | Val | Asn 575 | Phe |
| Phe | Arg | Met | Val | Ile 580 | Ser | Asn | Pro | Ala | Ala 585 | Thr | His | Gln | Asp 590 | Ile | Asp |
| Phe | Leu | Ile 595 | Glu | Glu | Ile | Glu | Arg 600 | Leu | Gly | Gln | Asp | Leu 605 | | | |

(2) INFORMATION FOR SEQ ID NO:10:

(i) SEQUENCE CHARACTERISTICS:
    (A) LENGTH: 2100 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:10:

```
AGCTCGCCCG CAGCTCGCAC TCGCAGGCGA CCTGCTCCAG TCTCCAAAGC CGATGGCATC    60
TCCGGGCTCT GGCTTTTGGT CTTTCGGGTC GGAAGATGGC TCTGGGGATT CCGAGAATCC   120
CGGCACAGCG CGAGCCTGGT GCCAAGTGGC TCAGAAGTTC ACGGGCGGCA TCGGAAACAA   180
ACTGTGCGCC CTGCTCTACG GAGACGCCGA GAAGCCGGCG GAGAGCGGCG GGAGCCAACC   240
CCCGCGGGCC GCCGCCCGGA AGGCCGCCTG CGCCTGCGAC CAGAAGCCCT GCAGCTGCTC   300
CAAAGTGGAT GTCAACTACG CGTTTCTCCA TGCAACAGAC CTGCTGCCGG CGTGTGATGG   360
AGAAAGGCCC ACTTTGGCGT TCTGCAAGA TGTTATGAAC ATTTTACTTC AGTATGTGGT   420
GAAAAGTTTC GATAGATCAA CCAAAGTGAT TGATTTCCAT TATCCTAATG AGCTTCTCCA   480
AGAATATAAT TGGGAATTGG CAGACCAACC ACAAAATTTG GAGGAAATTT TGATGCATTG   540
CCAAACAACT CTAAAATATG CAATTAAAAC AGGGCATCCT AGATACTTCA ATCAACTTTC   600
TACTGGTTTG GATATGGTTG GATTAGCAGC AGACTGGCTG ACATCAACAG CAAATACTAA   660
CATGTTCACC TATGAAATTG CTCCAGTATT TGTGCTTTTG GAATATGTCA CACTAAAGAA   720
AATGAGAGAA ATCATTGGCT GGCCAGGGGG CTCTGGCGAT GGGATATTTT CTCCCGGTGG   780
```

```
CGCCATATCT  AACATGTATG  CCATGATGAT  CGCACGCTTT  AAGATGTTCC  CAGAAGTCAA    840
GGAGAAAGGA  ATGGCTGCTC  TTCCCAGGCT  CATTGCCTTC  ACGTCTGAAC  ATAGTCATTT    900
TTCTCTCAAG  AAGGGAGCTG  CAGCCTTAGG  GATTGGAACA  GACAGCGTGA  TTCTGATTAA    960
ATGTGATGAG  AGAGGGAAAA  TGATTCCATC  TGATCTTGAA  AGAAGGATTC  TTGAAGCCAA   1020
ACAGAAAGGG  TTTGTTCCTT  TCCTCGTGAG  TGCCACAGCT  GGAACCACCG  TGTACGGAGC   1080
ATTTGACCCC  CTCTTAGCTG  TCGCTGACAT  TTGCAAAAAG  TATAAGATCT  GGATGCATGT   1140
GGATGCAGCT  TGGGGTGGGG  GATTACTGAT  GTCCCGAAAA  CACAAGTGGA  AACTGAGTGG   1200
CGTGGAGAGG  GCCAACTCTG  TGACGTGGAA  TCCACACAAG  ATGATGGGAG  TCCCTTTGCA   1260
GTGCTCTGCT  CTCCTGGTTA  GAGAAGAGGG  ATTGATGCAG  AATTGCAACC  AAATGCATGC   1320
CTCCTACCTC  TTTCAGCAAG  ATAAACATTA  TGACCTGTCC  TATGACACTG  GAGACAAGGC   1380
CTTACAGTGC  GGACGCCACG  TTGATGTTTT  TAAACTATGG  CTGATGTGGA  GGGCAAAGGG   1440
GACTACCGGG  TTTGAAGCGC  ATGTTGATAA  ATGTTTGGAG  TTGGCAGAGT  ATTTATACAA   1500
CATCATAAAA  AACCGAGAAG  GATATGAGAT  GGTGTTTGAT  GGGAAGCCTC  AGCACACAAA   1560
TGTCTGCTTC  TGGTACATTC  CTCCAAGCTT  GCGTACTCTG  GAAGACAATG  AAGAGAGAAT   1620
GAGTCGCCTC  TCGAAGGTGG  CTCCAGTGAT  TAAAGCCAGA  ATGATGGAGT  ATGGAACCAC   1680
AATGGTCAGC  TACCAACCCT  TGGGAGACAA  GGTCAATTTC  TTCCGCATGG  TCATCTCAAA   1740
CCCAGCGGCA  ACTCACCAAG  ACATTGACTT  CCTGATTGAA  GAAATAGAAC  GCCTTGGACA   1800
AGATTTATAA  TAACCTTGCT  CACCAAGCTG  TTCCACTTCT  CTAGGTAGAC  AATTAAGTTG   1860
TCACAAACTG  TGTGAATGTA  TTTGTAGTTT  GTTCCAAAGT  AAATCTATTT  CTATATTGTG   1920
GTGTCAAAGT  AGAGTTTAAA  AATTAAACAA  AAAAGACATT  GCTCCTTTTA  AAAGTCCTTT   1980
CTTAAGTTTA  GAATACCTCT  CTAAGAATTC  GTGACAAAAG  GCTATGTTCT  AATCAATAAG   2040
GAAAAGCTTA  AAATTGTTAT  AAATACTTCC  CTTACTTTTA  ATATAGTGTG  CAAAGCAAAC   2100
```

( 2 ) INFORMATION FOR SEQ ID NO:11:

( i ) SEQUENCE CHARACTERISTICS:
        ( A ) LENGTH: 585 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Met  Ala  Ser  Pro  Gly  Ser  Gly  Phe  Trp  Ser  Phe  Gly  Ser  Glu  Asp  Gly
 1              5                        10                       15

Ser  Gly  Asp  Ser  Glu  Asn  Pro  Gly  Thr  Ala  Arg  Ala  Trp  Cys  Gln  Val
               20                        25                       30

Ala  Gln  Lys  Phe  Thr  Gly  Gly  Ile  Gly  Asn  Lys  Leu  Cys  Ala  Leu  Leu
          35                        40                       45

Tyr  Gly  Asp  Ala  Glu  Lys  Pro  Ala  Glu  Ser  Gly  Gly  Ser  Gln  Pro  Pro
     50                        55                       60

Arg  Ala  Ala  Ala  Arg  Lys  Ala  Ala  Cys  Ala  Cys  Asp  Gln  Lys  Pro  Cys
65                        70                       75                       80

Ser  Cys  Ser  Lys  Val  Asp  Val  Asn  Tyr  Ala  Phe  Leu  His  Ala  Thr  Asp
                    85                        90                       95

Leu  Leu  Pro  Ala  Cys  Asp  Gly  Glu  Arg  Pro  Thr  Leu  Ala  Phe  Leu  Gln
               100                       105                      110

Asp  Val  Met  Asn  Ile  Leu  Leu  Gln  Tyr  Val  Val  Lys  Ser  Phe  Asp  Arg
```

```
                        115                          120                          125
Ser   Thr   Lys   Val   Ile   Asp   Phe   His   Tyr   Pro   Asn   Glu   Leu   Leu   Gln   Glu
      130                          135                          140

Tyr   Asn   Trp   Glu   Leu   Ala   Asp   Gln   Pro   Gln   Asn   Leu   Glu   Glu   Ile   Leu
145                          150                          155                          160

Met   His   Cys   Gln   Thr   Thr   Leu   Lys   Tyr   Ala   Ile   Lys   Thr   Gly   His   Pro
                        165                          170                          175

Arg   Tyr   Phe   Asn   Gln   Leu   Ser   Thr   Gly   Leu   Asp   Met   Val   Gly   Leu   Ala
                  180                          185                          190

Ala   Asp   Trp   Leu   Thr   Ser   Thr   Ala   Asn   Thr   Asn   Met   Phe   Thr   Tyr   Glu
            195                          200                          205

Ile   Ala   Pro   Val   Phe   Val   Leu   Leu   Glu   Tyr   Val   Thr   Leu   Lys   Lys   Met
      210                          215                          220

Arg   Glu   Ile   Ile   Gly   Trp   Pro   Gly   Gly   Ser   Gly   Asp   Gly   Ile   Phe   Ser
225                          230                          235                          240

Pro   Gly   Gly   Ala   Ile   Ser   Asn   Met   Tyr   Ala   Met   Met   Ile   Ala   Arg   Phe
                        245                          250                          255

Lys   Met   Phe   Pro   Glu   Val   Lys   Glu   Lys   Gly   Met   Ala   Ala   Leu   Pro   Arg
                  260                          265                          270

Leu   Ile   Ala   Phe   Thr   Ser   Glu   His   Ser   His   Phe   Ser   Leu   Lys   Lys   Gly
            275                          280                          285

Ala   Ala   Ala   Leu   Gly   Ile   Gly   Thr   Asp   Ser   Val   Ile   Leu   Ile   Lys   Cys
      290                          295                          300

Asp   Glu   Arg   Gly   Lys   Met   Ile   Pro   Ser   Asp   Leu   Glu   Arg   Arg   Ile   Leu
305                          310                          315                          320

Glu   Ala   Lys   Gln   Lys   Gly   Phe   Val   Pro   Phe   Leu   Val   Ser   Ala   Thr   Ala
                        325                          330                          335

Gly   Thr   Thr   Val   Tyr   Gly   Ala   Phe   Asp   Pro   Leu   Leu   Ala   Val   Ala   Asp
                  340                          345                          350

Ile   Cys   Lys   Lys   Tyr   Lys   Ile   Trp   Met   His   Val   Asp   Ala   Ala   Trp   Gly
            355                          360                          365

Gly   Gly   Leu   Leu   Met   Ser   Arg   Lys   His   Lys   Trp   Lys   Leu   Ser   Gly   Val
      370                          375                          380

Glu   Arg   Ala   Asn   Ser   Val   Thr   Trp   Asn   Pro   His   Lys   Met   Met   Gly   Val
385                          390                          395                          400

Pro   Leu   Gln   Cys   Ser   Ala   Leu   Leu   Val   Arg   Glu   Glu   Gly   Leu   Met   Gln
                        405                          410                          415

Asn   Cys   Asn   Gln   Met   His   Ala   Ser   Tyr   Leu   Phe   Gln   Gln   Asp   Lys   His
                  420                          425                          430

Tyr   Asp   Leu   Ser   Tyr   Asp   Thr   Gly   Asp   Lys   Ala   Leu   Gln   Cys   Gly   Arg
            435                          440                          445

His   Val   Asp   Val   Phe   Lys   Leu   Trp   Leu   Met   Trp   Arg   Ala   Lys   Gly   Thr
      450                          455                          460

Thr   Gly   Phe   Glu   Ala   His   Val   Asp   Lys   Cys   Leu   Glu   Leu   Ala   Glu   Tyr
465                          470                          475                          480

Leu   Tyr   Asn   Ile   Ile   Lys   Asn   Arg   Glu   Gly   Tyr   Glu   Met   Val   Phe   Asp
                        485                          490                          495

Gly   Lys   Pro   Gln   His   Thr   Asn   Val   Cys   Phe   Trp   Tyr   Ile   Pro   Pro   Ser
                  500                          505                          510

Leu   Arg   Thr   Leu   Glu   Asp   Asn   Glu   Glu   Arg   Met   Ser   Arg   Leu   Ser   Lys
            515                          520                          525

Val   Ala   Pro   Val   Ile   Lys   Ala   Arg   Met   Met   Glu   Tyr   Gly   Thr   Thr   Met
      530                          535                          540
```

```
Val  Ser  Tyr  Gln  Pro  Leu  Gly  Asp  Lys  Val  Asn  Phe  Phe  Arg  Met  Val
545                      550                 555                           560

Ile  Ser  Asn  Pro  Ala  Ala  Thr  His  Gln  Asp  Ile  Asp  Phe  Leu  Ile  Glu
                    565                      570                      575

Glu  Ile  Glu  Arg  Leu  Gly  Gln  Asp  Leu
                580                 585
```

( 2 ) INFORMATION FOR SEQ ID NO:12:

( i ) SEQUENCE CHARACTERISTICS:
        ( A ) LENGTH: 585 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Met  Ala  Ser  Pro  Gly  Ser  Gly  Phe  Trp  Ser  Phe  Gly  Ser  Glu  Asp  Gly
1                   5                   10                      15

Ser  Gly  Asp  Pro  Glu  Asn  Pro  Gly  Thr  Ala  Arg  Ala  Trp  Cys  Gln  Val
                20                  25                      30

Ala  Gln  Lys  Phe  Thr  Gly  Gly  Ile  Gly  Asn  Lys  Leu  Cys  Ala  Leu  Leu
           35                      40                      45

Tyr  Gly  Asp  Ser  Glu  Lys  Pro  Ala  Glu  Ser  Gly  Gly  Ser  Val  Thr  Ser
     50                  55                      60

Arg  Ala  Ala  Thr  Arg  Lys  Val  Ala  Cys  Thr  Cys  Asp  Gln  Lys  Pro  Cys
65                   70                  75                            80

Ser  Cys  Pro  Lys  Gly  Asp  Val  Asn  Tyr  Ala  Leu  Leu  His  Ala  Thr  Asp
                85                  90                      95

Leu  Leu  Pro  Ala  Cys  Glu  Gly  Glu  Arg  Pro  Thr  Leu  Ala  Phe  Leu  Gln
               100                 105                     110

Asp  Val  Met  Asn  Ile  Leu  Leu  Gln  Tyr  Val  Val  Lys  Ser  Phe  Asp  Arg
          115                      120                     125

Ser  Thr  Lys  Val  Ile  Asp  Phe  His  Tyr  Pro  Asn  Glu  Leu  Leu  Gln  Glu
     130                      135                     140

Tyr  Asn  Trp  Glu  Leu  Ala  Asp  Gln  Pro  Gln  Asn  Leu  Glu  Glu  Ile  Leu
145                      150                     155                      160

Thr  His  Cys  Gln  Thr  Thr  Leu  Lys  Tyr  Ala  Ile  Lys  Thr  Gly  His  Pro
               165                      170                     175

Arg  Tyr  Phe  Asn  Gln  Leu  Ser  Thr  Gly  Leu  Asp  Met  Val  Gly  Leu  Ala
               180                      185                     190

Ala  Asp  Trp  Leu  Thr  Ser  Thr  Ala  Asn  Thr  Asn  Met  Phe  Thr  Tyr  Glu
          195                      200                     205

Ile  Ala  Pro  Val  Phe  Val  Leu  Leu  Glu  Tyr  Val  Thr  Leu  Lys  Lys  Met
     210                      215                     220

Arg  Glu  Ile  Ile  Gly  Trp  Pro  Gly  Gly  Ser  Gly  Asp  Gly  Ile  Phe  Ser
225                      230                     235                      240

Pro  Gly  Gly  Ala  Ile  Ser  Asn  Met  Tyr  Ala  Met  Leu  Ile  Ala  Arg  Tyr
               245                      250                     255

Lys  Met  Phe  Pro  Glu  Val  Lys  Glu  Lys  Gly  Met  Ala  Ala  Val  Pro  Arg
               260                      265                     270

Leu  Ile  Ala  Phe  Thr  Ser  Glu  His  Ser  His  Phe  Ser  Leu  Lys  Lys  Gly
          275                      280                     285

Ala  Ala  Ala  Leu  Gly  Ile  Gly  Thr  Asp  Ser  Val  Ile  Leu  Ile  Lys  Cys
     290                      295                     300

Asp  Glu  Arg  Gly  Lys  Met  Ile  Pro  Ser  Asp  Leu  Glu  Arg  Arg  Ile  Leu
```

|  | 305 |  |  |  |  | 310 |  |  |  |  | 315 |  |  |  |  | 320 |
|---|---|---|---|---|---|---|---|---|---|---|---|---|---|---|---|---|
| Glu | Val | Lys | Gln | Lys<br>325 | Gly | Phe | Val | Pro | Phe<br>330 | Leu | Val | Ser | Ala | Thr<br>335 | Ala |
| Gly | Thr | Thr | Val<br>340 | Tyr | Gly | Ala | Phe | Asp<br>345 | Pro | Leu | Leu | Ala | Val<br>350 | Ala | Asp |
| Ile | Cys | Lys<br>355 | Lys | Tyr | Lys | Ile | Trp<br>360 | Met | His | Val | Asp | Ala<br>365 | Ala | Trp | Gly |
| Gly | Gly<br>370 | Leu | Leu | Met | Ser | Arg<br>375 | Lys | His | Lys | Trp | Lys<br>380 | Leu | Asn | Gly | Val |
| Glu<br>385 | Arg | Ala | Asn | Ser | Val<br>390 | Thr | Trp | Asn | Pro | His<br>395 | Lys | Met | Met | Gly | Val<br>400 |
| Pro | Leu | Gln | Cys | Ser<br>405 | Ala | Leu | Leu | Val | Arg<br>410 | Glu | Glu | Gly | Leu | Met<br>415 | Gln |
| Ser | Cys | Asn | Gln<br>420 | Met | His | Ala | Ser | Tyr<br>425 | Leu | Phe | Gln | Gln | Asp<br>430 | Lys | His |
| Tyr | Asp | Leu<br>435 | Ser | Tyr | Asp | Thr | Gly<br>440 | Asp | Lys | Ala | Leu | Gln<br>445 | Cys | Gly | Arg |
| His | Val<br>450 | Asp | Val | Phe | Lys | Leu<br>455 | Trp | Leu | Met | Trp | Arg<br>460 | Ala | Lys | Gly | Thr |
| Thr<br>465 | Gly | Phe | Glu | Ala | His<br>470 | Ile | Asp | Lys | Cys | Leu<br>475 | Glu | Leu | Ala | Glu | Tyr<br>480 |
| Leu | Tyr | Asn | Ile | Ile<br>485 | Lys | Asn | Arg | Glu | Gly<br>490 | Tyr | Glu | Met | Val | Phe<br>495 | Asp |
| Gly | Lys | Pro | Gln<br>500 | His | Thr | Asn | Val | Cys<br>505 | Phe | Trp | Phe | Val | Pro<br>510 | Pro | Ser |
| Leu | Arg | Val<br>515 | Leu | Glu | Asp | Asn | Glu<br>520 | Glu | Arg | Met | Ser | Arg<br>525 | Leu | Ser | Lys |
| Val | Ala<br>530 | Pro | Val | Ile | Lys | Ala<br>535 | Arg | Met | Met | Glu | Tyr<br>540 | Gly | Thr | Thr | Met |
| Val<br>545 | Ser | Tyr | Gln | Pro | Leu<br>550 | Gly | Asp | Lys | Val | Asn<br>555 | Phe | Phe | Arg | Met | Val<br>560 |
| Ile | Ser | Asn | Pro | Ala<br>565 | Ala | Thr | His | Gln | Asp<br>570 | Ile | Asp | Phe | Leu | Ile<br>575 | Glu |
| Glu | Ile | Glu | Arg<br>580 | Leu | Gly | Gln | Asp | Leu<br>585 |  |  |  |  |  |  |  |

( 2 ) INFORMATION FOR SEQ ID NO:13:

( i ) SEQUENCE CHARACTERISTICS:
        ( A ) LENGTH: 585 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

| Met<br>1 | Ala | Ser | Pro | Gly<br>5 | Ser | Gly | Phe | Trp | Ser<br>10 | Phe | Gly | Ser | Glu | Asp<br>15 | Gly |
|---|---|---|---|---|---|---|---|---|---|---|---|---|---|---|---|
| Ser | Gly | Asp | Ser<br>20 | Glu | Asn | Pro | Gly | Thr<br>25 | Ala | Arg | Ala | Trp | Cys<br>30 | Gln | Val |
| Ala | Gln | Lys<br>35 | Phe | Thr | Gly | Gly | Ile<br>40 | Gly | Asn | Lys | Leu | Cys<br>45 | Ala | Leu | Leu |
| Tyr | Gly<br>50 | Asp | Ala | Glu | Lys | Pro<br>55 | Ala | Glu | Ser | Gly | Gly<br>60 | Ser | Gln | Pro | Pro |
| Arg<br>65 | Ala | Ala | Ala | Arg | Lys<br>70 | Ala | Ala | Cys | Ala | Cys<br>75 | Asp | Gln | Lys | Pro | Cys<br>80 |

|     |     |     |     |     |     |     |     |     |     |     |     |     |     |
|-----|-----|-----|-----|-----|-----|-----|-----|-----|-----|-----|-----|-----|-----|
| Ser | Cys | Ser | Lys<br>85 | Val | Asp | Val | Asn | Tyr | Ala<br>90 | Phe | Leu | His | Ala | Thr<br>95 | Asp |
| Leu | Leu | Pro | Ala<br>100 | Cys | Asp | Gly | Glu | Arg<br>105 | Pro | Thr | Leu | Ala | Phe<br>110 | Leu | Gln |
| Asp | Val | Met<br>115 | Asn | Ile | Leu | Leu | Gln<br>120 | Tyr | Val | Val | Lys | Ser<br>125 | Phe | Asp | Arg |
| Ser | Thr | Lys<br>130 | Val | Ile | Asp | Phe<br>135 | His | Tyr | Pro | Asn | Glu<br>140 | Leu | Leu | Gln | Glu |
| Tyr<br>145 | Asn | Trp | Glu | Leu | Ala<br>150 | Asp | Gln | Pro | Gln | Asn<br>155 | Leu | Glu | Glu | Ile | Leu<br>160 |
| Met | His | Cys | Gln | Thr<br>165 | Thr | Leu | Lys | Tyr | Ala<br>170 | Ile | Lys | Thr | Gly | His<br>175 | Pro |
| Arg | Tyr | Phe | Asn<br>180 | Gln | Leu | Ser | Thr | Gly<br>185 | Leu | Asp | Met | Val | Gly<br>190 | Leu | Ala |
| Ala | Asp | Trp<br>195 | Leu | Thr | Ser | Thr | Ala<br>200 | Asn | Thr | Asn | Met | Phe<br>205 | Thr | Tyr | Glu |
| Ile | Ala<br>210 | Pro | Val | Phe | Val | Leu<br>215 | Leu | Glu | Tyr | Val | Thr<br>220 | Leu | Lys | Lys | Met |
| Arg<br>225 | Glu | Ile | Ile | Gly | Trp<br>230 | Pro | Gly | Gly | Ser | Gly<br>235 | Asp | Gly | Ile | Phe | Ser<br>240 |
| Pro | Gly | Gly | Ala | Ile<br>245 | Ser | Asn | Met | Tyr | Ala<br>250 | Met | Met | Ile | Ala | Arg<br>255 | Phe |
| Lys | Met | Phe | Pro<br>260 | Glu | Val | Lys | Glu | Lys<br>265 | Gly | Met | Ala | Ala | Leu<br>270 | Pro | Arg |
| Leu | Ile | Ala<br>275 | Phe | Thr | Ser | Glu | His<br>280 | Ser | His | Phe | Ser | Leu<br>285 | Lys | Lys | Gly |
| Ala | Ala<br>290 | Ala | Leu | Gly | Ile | Gly<br>295 | Thr | Asp | Ser | Val | Ile<br>300 | Leu | Ile | Lys | Cys |
| Asp<br>305 | Glu | Arg | Gly | Lys | Met<br>310 | Ile | Pro | Ser | Asp | Leu<br>315 | Glu | Arg | Arg | Ile | Leu<br>320 |
| Glu | Ala | Lys | Gln | Lys<br>325 | Gly | Phe | Val | Pro | Phe<br>330 | Leu | Val | Ser | Ala | Thr<br>335 | Ala |
| Gly | Thr | Thr | Val<br>340 | Tyr | Gly | Ala | Phe | Asp<br>345 | Pro | Leu | Leu | Ala | Val<br>350 | Ala | Asp |
| Ile | Cys | Lys<br>355 | Lys | Tyr | Lys | Ile | Trp<br>360 | Met | His | Val | Asp | Ala<br>365 | Ala | Trp | Gly |
| Gly | Gly<br>370 | Leu | Leu | Met | Ser | Arg<br>375 | Lys | His | Lys | Trp | Lys<br>380 | Leu | Ser | Gly | Val |
| Glu<br>385 | Arg | Ala | Asn | Ser | Val<br>390 | Thr | Trp | Asn | Pro | His<br>395 | Lys | Met | Met | Gly | Val<br>400 |
| Pro | Leu | Gln | Cys | Ser<br>405 | Ala | Leu | Leu | Val | Arg<br>410 | Glu | Glu | Gly | Leu | Met<br>415 | Gln |
| Asn | Cys | Asn | Gln<br>420 | Met | His | Ala | Ser | Tyr<br>425 | Leu | Phe | Gln | Gln | Asp<br>430 | Lys | His |
| Tyr | Asp | Leu | Ser<br>435 | Tyr | Asp | Thr | Gly | Asp<br>440 | Lys | Ala | Leu | Gln | Cys<br>445 | Gly | Arg |
| His | Val | Asp<br>450 | Val | Phe | Lys | Leu | Trp<br>455 | Leu | Met | Trp | Arg | Ala<br>460 | Lys | Gly | Thr |
| Thr<br>465 | Gly | Phe | Glu | Ala | His<br>470 | Val | Asp | Lys | Cys | Leu<br>475 | Glu | Leu | Ala | Glu | Tyr<br>480 |
| Leu | Tyr | Asn | Ile | Ile<br>485 | Lys | Asn | Arg | Glu | Gly<br>490 | Tyr | Glu | Met | Val | Phe<br>495 | Asp |
| Gly | Lys | Pro | Gln | His | Thr | Asn | Val | Cys | Phe | Trp | Tyr | Ile | Pro | Pro | Ser |

|   |   |   |   |   |   |   | 500 |   |   |   | 505 |   |   |   | 510 |   |   |
|---|---|---|---|---|---|---|---|---|---|---|---|---|---|---|---|---|---|
| Leu | Arg | Thr 515 | Leu | Glu | Asp | Asn | Glu | Glu | Arg | Met | Ser 520 | Arg 525 | Leu | Ser | Lys | | |
| Val | Ala 530 | Pro | Val | Ile | Lys | Ala 535 | Arg | Met | Met | Glu | Tyr 540 | Gly | Thr | Thr | Met | | |
| Val 545 | Ser | Tyr | Gln | Pro | Leu 550 | Gly | Asp | Lys | Val | Asn 555 | Phe | Phe | Arg | Met | Val 560 | | |
| Ile | Ser | Asn | Pro | Ala 565 | Ala | Thr | His | Gln | Asp 570 | Ile | Asp | Phe | Leu | Ile 575 | Glu | | |
| Glu | Ile | Glu | Arg 580 | Leu | Gly | Gln | Asp | Leu 585 |   |   |   |   |   |   |   | | |

CLONED GLUTAMIC ACID DECARBOXYLASE NUCLEIC ACIDS

This is division of application Ser. No. 08/135,849 filed Oct. 13, 1993 now U.S. Pat. No. 5,475,086, a continuation of Ser. No. 07/716,909 filed Jun. 18, 1991, now abandoned, which is a continuation-in-part of 07/586,536 filed Sep. 21, 1990.

The present invention was supported by Grant NS22256 from the National Institutes of Health. The United States Government has certain rights in this invention.

BACKGROUND OF THE INVENTION

1. Field of the Invention

The present invention relates to the use of recombinant DNA technology for the transformation of a host organism with glutamic acid decarboxylase$_{65}$ (GAD$_{65}$) for the expression of GAD$_{65}$ polypeptides. Also encompassed are methods of using GAD$_{65}$ polypeptides diagnostically and therapeutically in autoimmune disease.

2. Description of the Background Art

Insulin-dependent diabetes mellitus (IDDM; type I diabetes) is one of the most common metabolic disorders. In the United States, IDDM affects approximately one in 300 to 400 people, and epidemiological studies suggest that its incidence is increasing. The disease results from the autoimmune destruction of the insulin-producing β-cells of the pancreas. More specifically, the preonset stage is characterized by "insulitis", in which lymphocytes infiltrate the pancreatic islets and selectively destroy the β-cells. The typical IDDM presentation of hyperglycemia appears only after at least 80% of the insulin-producing β-cells are lost. The remaining β-cells are destroyed during the next few years.

Although insulin therapy allows most IDDM patients to lead normal lives, this replacement is imperfect and does not completely restore metabolic homeostasis. Thus, severe complications which result in dysfunctions of the eye, kidney, heart, and other organs are common in IDDM patients undergoing insulin therapy. Because of this, it is highly desirable to extend the latency period (e.g., through administration of immunosuppressant drugs) between the start of β-cell destruction and the actual requirement of insulin replacement (i.e., when 80% of the β-cells are destroyed). Therefore, a diagnostic test which determines the beginning of β-cell destruction would allow the clinician to administer immunosuppressant drugs (Silverstein, et al., *New England Journal of Medicine*, 31 9:599–604, 1988) to extend this latency period and thus significantly delay the onset of insulin replacement side effects.

Many IDDM patients have sera which contain antibodies to a 64 kD molecule (Baekkeskov, et al., *J. Clin. Invest.*, 79:926–934, 1987; Atkinson, et al., *Lancet*, 335:1357–1360, 1990), to islet cell cytoplasmic (ICA) molecules or islet cell surface (ICSA) molecules (Bottazzo, et al., *Lancet*, 1:668–672, 1980), or to insulin (Palmer, et al., *Science*, 222:1137–1139, 1983; Atkinson, et al., *Diabetes*, 35:894–898, 1986). Atkinson and coworkers (Atkinson, et al., Lancet, 335:1357–1360, 1990) have demonstrated that the presence of antibodies to the 64 kD molecule in human sera appears to be the earliest and most reliable indicator that onset of IDDM symptoms will eventually occur.

Recently, Baekkeskov and coworkers established that the 64 kD molecule and glutamic acid decarboxylase (GAD) have several antigenic epitopes in common and thus they may be identical or very similar molecules. Although this identification is an important finding, the use of this information as a diagnostic tool for predicting IDDM is quite cumbersome and limited unless knowledge of the molecular biology of GAD is known. Consequently, the cloning and subsequent production of large quantities of the 64 kD molecule, or a GAD molecule which is antigenically substantially identical to the 64 kD molecule, will allow the development of a diagnostic kit designed to predict IDDM. The present invention provides a means for accomplishing this result.

SUMMARY OF THE INVENTION

The present invention arose out of the discovery that recombinant DNA technology could be used to produce eukaryotic GAD$_{65}$ polypeptide and that GAD$_{65}$ polypeptide could be used in the diagnosis and therapy of patients with autoimmune disease. Particularly relevant is the use of cloned eukaryotic GAD$_{65}$ polypeptide in the diagnosis of patients having, or at risk of having, insulin-dependent diabetes mellitus (IDDM).

A major advantage of the present invention is that it provides the art with a ready source of eukaryotic GAD$_{65}$ polypeptide corresponding to that purified from natural sources, while avoiding the problems associated with the isolation of naturally occurring eukaryotic GAD$_{65}$ polypeptide when separating it from other eukaryotic non-GAD$_{65}$ polypeptides. This absence of other eukaryotic non-GAD$_{65}$ polypeptides is significant in that it allows the development of test systems which will only detect antibodies specifically reactive with GAD$_{65}$ polypeptides.

Another advantage of providing eukaryotic GAD$_{65}$ polypeptide in host cells is that by so doing, it is possible to obtain much larger quantities of the polypeptide than are currently practicably available from natural sources. As a consequence, not only is it possible to use the polypeptide of the invention to more accurately classify patients with such autoimmune diseases as IDDM, but it is also now possible to provide commercially useful quantities of GAD$_{65}$ polypeptide for use in diagnostic systems.

DESCRIPTION OF THE DRAWINGS

FIG. 2 DNA sequence and corresponding amino acid sequence for rat GAD$_{65}$.

FIG. 3 DNA sequence and corresponding amino acid sequence for human GAD$_{65}$.

FIG. 4 Comparison of rat GAD$_{65}$ and human GAD$_{65}$ amino acid sequences.

DETAILED DESCRIPTION OF THE INVENTION

Figure 1:
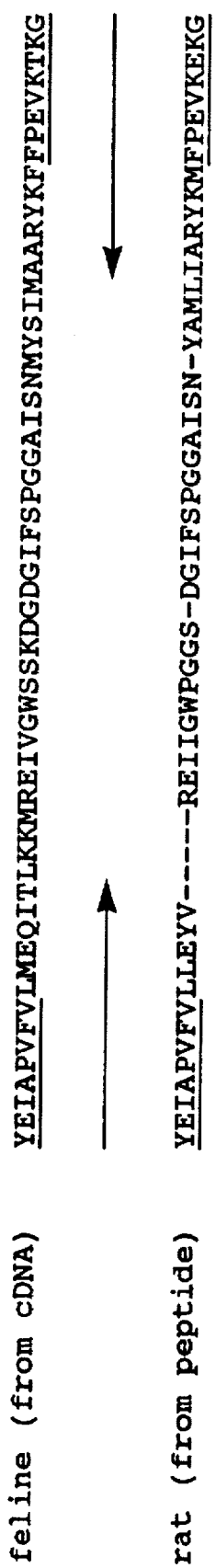
FIG. 1 Cloning strategy for obtaining GAD$_{65}$ and GAD$_{67}$ specific cDNA probes.

The present invention relates to the manipulation of genetic materials by recombinant procedures which make possible the production of polypeptides possessing part or all of the primary structural conformation for one or more of the epitopes for binding autoantibodies to glutamic acid decarboxylase$_{65}$ (GAD$_{65}$). These polypeptides are highly useful for the immunological detection of autoantibodies reactive with them, since such autoantibodies are indicative of autoimmune diseases such as insulin dependent diabetes mellitus and "stiff man" syndrome. These polypeptides can also be used for purposes of screening drugs, such as those that alter GAD function, and for generation of polyclonal and monoclonal antibodies which, in turn, can be used diagnostically to detect $GAD_{65}$.

The development of specific DNA sequences encoding eukaryotic $GAD_{65}$ polypeptide for splicing into DNA vectors can be accomplished using a variety of techniques. For example, alternative methods which can be employed include (1) the isolation of a double stranded DNA sequence from the genomic DNA of the eukaryote; (2) the chemical manufacture of a DNA sequence to provide the necessary codons for the polypeptide of interest; and (3) the in vitro synthesis of a double stranded DNA sequence by reverse transcription of mRNA isolated from a eukaryotic donor cell. In the latter case, a double stranded DNA complement of mRNA is eventually formed which is generally referred to as cDNA.

The manufacture of DNA sequences is frequently the method of choice when the entire sequence of amino acid residues of the desired polypeptide product is known. When the entire sequence of amino acid residues of the desired polypeptide is not known, the direct manufacture of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double stranded DNA or RNA probe sequences duplicating a sequence putatively present in the target cDNA may be employed in DNA/DNA hybridization procedures which are carried out on cloned copies of the cDNA which have been denatured into a single stranded form (Jay, et al., *Nucleic Acid Research*, 11:2325, 1983).

Hybridization procedures are useful for the screening of recombinant clones by using labeled mixed synthetic oligonucleotide probes wherein each is potentially the complete complement of a specific DNA sequence in the hybridization sample which includes a heterogeneous mixture of denatured double stranded DNA. For such screening, hybridization is preferably performed on either single stranded DNA or denatured double stranded DNA. These procedures are particularly useful in the detection of cDNA clones derived from sources where an extremely low amount of mRNA sequences relating to the polypeptide of interest are present. In other words, by using stringent hybridization conditions directed toward avoidance of non-specific binding, it is possible, for example, to allow the autoradiographic visualization of a specific cDNA done by the hybridization of the target DNA to that single probe in the mixture which is its complete complement (Wallace, et al., *Nucleic Acid Research*, 9:879, 1981).

In addition, a GAD cDNA library can be screened by injecting the various cDNAs into oocytes, allowing sufficient time for expression of the cDNA gene products to occur, and testing for the presence of the desired cDNA expression product, for example, by using antibody specific for $GAD_{65}$ polypeptide or by using functional assays for $GAD_{65}$ enzymatic activity.

Alternatively, a cDNA library can be screened indirectly for $GAD_{65}$ peptides having at least one epitope using antibodies to $GAD_{65}$ (Chang and Gottlieb, *J. Neurosci.*, 8:2123, 1988). Such antibodies can be either polyclonally or monoclonally derived and used to detect expression product indicative of the presence of $GAD_{65}$ cDNA. Preferred are antibodies directed to an epitope found in the first 100 amino acids of the N-terminal portion of $GAD_{65}$.

Of the three above-noted methods for developing specific DNA sequences for use in recombinant procedures, the use of genomic DNA isolates, is the least common This is especially true when it is desirable to obtain the microbial expression of mammalian polypeptides because of the presence of introns.

The present invention provides novel polypeptides of $GAD_{65}$ which have part or all of the primary structural conformation, that is, a continuous sequence of amino acid residues, having at least one epitope for antibodies to $GAD_{65}$.

It is possible to use the polypeptide fragments of file invention rather than intact $GAD_{65}$ to detect autoantibodies to $GAD_{65}$. The term "polypeptide," as applied to $GAD_{65}$ polypeptide, denotes any sequence of amino acids having an epitope for autoantibodies to $GAD_{65}$, wherein the sequence of amino acids is encoded by all or part of file cDNA sequences of the invention.

The polypeptides resulting from microbial expression of file DNA sequences of the invention can be further characterized by their freedom from association with other eukaryotic polypeptides or other contaminants which might otherwise be associated with $GAD_{65}$ in its natural cellular environment or in such extracellular fluids as plasma or urine.

Studies by file present inventors unequivocally establish that $GAD_{65}$ and GAD67 are encoded by distinct genes and are not produced, for example, by post-transcriptional or post-translational modification of a common genomic sequence. Evidence proving that $GAD_{65}$ and $GAD_{67}$ are encoded by different genes include: (a) the largest contiguous sequence of exact identity between $GAD_{65}$ and $GAD_{67}$ cDNAs is only 17 nucleotides in length, (b) cDNAs from $GAD_{65}$ and $GAD_{67}$ do not cross hybridize with each other's or with each other's mRNA under low stringency conditions (2.0×SSC, 0.01% SDS, 23° C.), and (c) $GAD_{65}$ and $GAD_{67}$ cDNAs do not cross hybridize with isolated genomic clones encoding $GAD_{67}$ and $GAD_{65}$, respectively.

The term "host" is meant to include not only prokaryotes, but also such eukaryotes as yeast, filamentous fungi, as well as plant and animal cells which can replicate and express an intron-free DNA sequence of eukaryotic $GAD_{65}$. However, prokaryotes are preferred as the host organism.

The term "prokaryotes" is meant to include all bacteria which can be transformed or transfected with the gene for the expression of $GAD_{65}$. Prokaryotic hosts may include gram negative as well as gram positive bacteria such as, for example, *E. coli*, *S. typhimurium*, *Serratia marcescens* and *Bacillus subtilis*.

A recombinant DNA molecule coding for the $GAD_{65}$ polypeptides can be used to transform or transfect the host using any of the techniques commonly known to those of ordinary skill in the art. Especially preferred is the use of a plasmid or a virus containing the $GAD_{65}$ coding sequence for purposes of prokaryotic transformation or transfection, respectively.

Methods for preparing fused, operably linked genes and expressing them in bacteria are well-known in the art (Maniatis, et al., *Molecular Cloning: A Laboratory Manual*, Cold Spring Harbor Laboratory, Cold Spring Harbor, N.Y., 1989). The genetic constructs and methods described therein can be utilized for expression of $GAD_{65}$ in prokaryotic hosts.

In general, expression vectors containing promotor sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The polypeptides of the invention can then be isolated from the grown medium, cellular lysates, or cellular membrane fractions.

The isolation and purification of the microbially expressed polypeptides of the invention may be by any conventional means such as, for example, preparative chromatographic separations and immunological separations such as those involving the use of monoclonal or polyclonal antibody.

By having provided the sequence of amino acid residues of $GAD_{65}$, the present invention provides for the manufacture of DNA sequences which code for the host expression of polypeptide analogs or derivatives of $GAD_{65}$ which differ from naturally-occurring forms in terms of the identity or location of one or more amino acid residues and which share some or all of the epitopes of naturally-occurring polypeptide forms.

The novel DNA sequences of the invention include all sequences useful in providing the expression in prokaryotic or eukaryotic host cells of polypeptides which have at least a part of the primary structural conformation for one or more epitopes capable of reacting with autoantibodies to $GAD_{65}$ which are comprehended by: (a) the DNA sequence as set forth in FIGS. 2 or 3 or their complementary strands; (b) DNA sequences which hybridize to DNA sequences defined in (a) or fragments thereof; and (c) DNA sequences which, but for the degeneracy of the genetic code, would hybridize to DNA sequences defined in (a) and (b) above. Specifically comprehended in (b) are genomic DNA sequences which encode allelic variant forms of $GAD_{65}$. Part (c) specifically comprehends the manufacture of DNA sequences which encode $GAD_{65}$, $GAD_{65}$ fragments, and $GAD_{65}$ analogs wherein the DNA sequences thereof may incorporate codons which facilitate translation of mRNA in non-vertebrate hosts.

Since the cDNA sequence of the invention encodes essentially the entire human or rat $GAD_{65}$ molecule, it is now a matter of routine to prepare, subclone, and express smaller polypeptide fragments of cDNA from this or a corresponding cDNA sequence which would encode as few as one epitope for autoantibodies to human or rat $GAD_{65}$. The presence of such an epitope on a cloned polypeptide can then be confirmed using, for example, sera from a patient with autoantibodies to $GAD_{65}$. An example of such a smaller peptide is the first approximately 100 amino acids from the N-terminus of $GAD_{65}$ (shown in FIG. 3). This amino acid sequence is essentially absent from $GAD_{67}$.

The $GAD_{65}$ of the invention is particularly suited for use in immunoassays in which it can be utilized in liquid phase or bound to a solid phase carrier. In addition, $GAD_{65}$ used in these assays can be detectably labeled in various ways.

Examples of immunoassays which can utilize the $GAD_{65}$ of the invention are competitive and non-competitive immunoassays in either a direct or indirect format. Examples of such immunoassays are the radioimmunoassay (RIA), the sandwich (immunometric assay) and the Western blot assay. Detection of antibodies which bind to the $GAD_{65}$ of the invention can be done utilizing immunoassays which run in either the forward, reverse, or simultaneous modes, including immunohistochemical assays on physiological samples. The concentration of $GAD_{65}$ which is used will vary depending on the type of immunoassay and nature of the detectable label which is used. However, regardless of the type of immunoassay which is used, the concentration of $GAD_{65}$ utilized can be readily determined by one of ordinary skill in the art using routine experimentation.

The $GAD_{65}$ of the invention can be bound to many different carries and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding $GAD_{65}$, or will be able to ascertain such, using routine experimentation.

There am many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

Alternatively, the polypeptide of the invention can be used to detect antibodies to $GAD_{65}$ by measuring GAD enzymatic activity. For example, $GAD_{65}$ and a specimen suspected of having antibodies to $GAD_{65}$ can be incubated for a period of time and under conditions sufficient to allow binding to occur between $GAD_{65}$ and the antibodies. The reaction product is precipitated and then tested for GAD enzymatic activity.

For purposes of the invention, the antibody which binds to $GAD_{65}$ of the invention may be present in various biological fluids and tissues. Any sample containing a detectable amount of antibodies to $GAD_{65}$ can be used. Normally, a sample is a liquid such as urine, saliva, cerebrospinal fluid, blood, serum and the like, or a solid or semi-solid such as tissue, feces and the like.

The materials for use in the assay of the invention are ideally suited for the preparation of a kit. Such a kit may comprise a carrier means being compartmentalized to receive in close confinement one or more container means such as vials, tubas and the like, each of the container means comprising one of the separate elements to be used in the method. For example, one of the container means may comprise $GAD_{65}$ bound to a carrier. A second container may comprise soluble, detectably-labeled second antibody, in lyophilized form or in solution.

In addition, the carrier means may also contain a plurality of containers each of which comprises different, predetermined mounts of $GAD_{65}$. These latter containers can then be used to prepare a standard curve into which can be interpolated the results obtained from the sample containing the unknown amount of autoantibodies to $GAD_{65}$.

In using the kit all the user has to do is add, to a container, a premeasured amount of a sample containing a measurable, yet unknown mount of autoantibodies to $GAD_{65}$ to be detected, a premeasured mount of carrier-bound $GAD_{65}$ present in the first container, and a premeasured amount of the detectably labeled second antibody present in the second container. Alternatively, the non-detectably labeled $GAD_{65}$ can be provided attached to the container to which the sample and the detectably labeled second antibody are added. After an appropriate time for incubation, an immune complex is formed and is separated from the supernatant fluid, and the immune complex or the supernatant fluid are detected, as by radioactive counting or addition of an enzyme substrate, and color development.

The term "ameliorate" denotes a lessening of the detrimental effect of the autoimmune response in the patient receiving therapy. The term "therapeutically effective" means that the amount of $GAD_{65}$ polypeptide used is of sufficient quantity to ameliorate the cause of disease due to the autoimmune response.

The recombinant $GAD_{65}$ polypeptides of the invention can also be used therapeutically in patients having an autoimmune response to $GAD_{65}$. Such therapy can be accomplished by, for example, the administration of recombinant $GAD_{65}$ polypeptide. Such administration can utilize unlabeled as well as labeled $GAD_{65}$ polypeptide. When unlabeled $GAD_{65}$ polypeptide is utilized advantageously, it would be in a form wherein, for example, the $GAD_{65}$ polypeptides are in fragments which are too small to stimulate an immune response, but large enough to bind, or block, the continuance of the autoimmune response. For example, $GAD_{65}$ could be digested enzymatically into epitope-sized peptides (typically 5-12 amino acids in length) and thereby bind to Fab binding portions present in the body fluids, or on the surface of immune cells, of the patient with autoimmune disease.

Alternatively, the recombinant $GAD_{65}$ polypeptides of the invention could be administered labeled with a therapeutic agent. These agents can be coupled either directly or indirectly to the $GAD_{65}$ polypeptides of the invention. One example of indirect coupling is by use of a spacer moiety. These spacer moieties, in turn, can be either insoluble or soluble (Diener, et al., Science, 231:148, 1986) and can be selected to enable drug release from the $GAD_{65}$ polypeptide at the target site. Examples of therapeutic agents which can be coupled to the $GAD_{65}$ polypeptides of the invention for immunotherapy are drugs, radioisotopes, lectins, and toxins.

The drugs with which can be conjugated to the $GAD_{65}$ polypeptides of the invention include compounds which are classically referred to as drugs such as mitomycin C, daunorubicin, and vinblastine.

In using radioisotopically conjugated $GAD_{65}$ polypeptides of the invention for immunotherapy, certain isotopes may be more preferable than others depending on such factors as leukocyte distribution as well as stability and emission. Depending on the autoimmune response, some emitters may be preferable to others. In general, $\alpha$ and $\beta$ particle-emitting radioisotopes are preferred in immunotherapy. Preferred are short range, high energy $\alpha$ emitters such as $^{212}Bi$. Examples of radioisotopes which can be bound to the $GAD_{65}$ polypeptides of the invention for therapeutic purposes are $^{125}I, ^{131}I, ^{90}Y, ^{67}Cu, ^{212}Bi, ^{211}At, ^{212}Pb, ^{47}Sc, ^{190}Pd$ and $^{188}Re$.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is accomplished by binding the $\alpha$-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by Corynebacterium diphtheria which can be used therapeutically. This toxin consists of an $\alpha$ and $\beta$ subunit which under proper conditions can be separated. The toxic A component can be bound to $GAD_{65}$ polypeptide and used for site specific delivery to a leukocyte expressing a receptor for $GAD_{65}$ polypeptide.

Other therapeutic agents which can be coupled to the $GAD_{65}$ polypeptides of the invention, as well as ex vivo and in vivo therapeutic protocols, are known, or can be easily ascertained, by those of ordinary skill in the art.

The present invention also relates to a polypeptide which can be administered therapeutically to ameliorate the disease process in patients having, or at risk of having, this disease. The conventional single-letter code used to represent the various amino acids relates as follows:

| | | | |
|---|---|---|---|
| Phe: F | Leu: L | Ile: I | Met: M |
| Val: V | Ser: S | Pro: P | Thr: T |
| Ala: A | Tyr: Y | His: H | Gln: Q |
| Asn: N | Lys: K | Asp: D | Glu: E |
| Cys: C | Trp: W | Arg: R | Gly: G |

The polypeptide sequence of the invention was identified by comparing the amino acid sequences of human $GAD_{65}$, human $GAD_{67}$, and the P2-C protein of the picornavirus, coxsackie virus. The P2-C polynucleotide plays a role in the virus membrane bound replication complex. These analyses established the presence of an extensive sequence similarity between both $GAD_{65}$ molecules and the coxsackie virus. A core polypeptide of six contiguous amino acid residues of the $GAD_{65}$ and P2-C polypeptide are identical in amino add sequence. Indeed, of the 24 amino acids in the polypeptide, 19 are identical or conserved. In addition, there also exists a high charge density and the presence of a proline residue which would render this region highly antigenic (see Table 1).

TABLE 1

| PROTEIN | AMINO ACID SEQUENCE |
|---|---|
| Human GAD$_{67}$ | 258 S I M A A R Y K Y F P E V K T K G M A A V P K L 281 (SEQ ID NO:01) |
| Human GAD$_{65}$ | 250 A M M I A R F K M F P E V K E K G M A A L P R L 273 (SEQ ID NO:4) |
| Coxsackie Virus P2-C | 26 P I E W L K V K I L P E V K E K H E F — L S R L 50 (SEQ ID NO:05) |

In Table 1, the solid line encloses identical amino acids whereas the dashed line encloses amino acid residues with similar charge, polarity, or hydrophobicity.

The discovery of this common polypeptide region supports an etiologic role for "molecular mimicry" in the precipitation of diabetes. Thus, where a patient genetically susceptible to IDDM is infected by a coxsackie virus, the immune response to the coxsackie virus polypeptide results in a cross reactive immune response to the similar GAD sequence in the patient's β-cells. The immunological response is maintained by the antigenically similar GAD polypeptides resulting in the eventual destruction of the β-cells and the subsequent presentation of IDDM.

At present, it is believed that the elimination of pancreatic β-cells is mediated by a cellular autoimmune response. Consequently, a polypeptide of the invention should have the capability of blocking such cellular autoimmune response. Because of the complexity of autoimmune disease, it is possible to envision numerous possible therapeutic modalities which would allow the polypeptides of the invention to be used to ameliorate such diseases. Thus, it may be possible to utilize the polypeptides of the invention to block recognition by a specific T cell receptor (TCR) or an MHC receptor presenting an autoimmune antigen on the surface of an antigen presenting cell (APC). The inhibition of such recognition might occur, for example, by providing the patient with the polypeptide of the invention which, in turn, could displace the autoimmune antigen being presented in the antigen-cleft of the MHC receptor or, possibly, by direct interaction with the appropriate TCR on the surface of a T-helper cell. This latter therapeutic approach of direct interaction with the TCR could be achieved through induction of high-zone tolerance by use of high concentrations of soluble polypeptide.

Alternatively, the polypeptides of the invention could be used to stimulate a T-suppressor cell population in order to restore self-recognition and, thereby, ameliorate the autoimmune disease. Stimulation of T-suppressor cell populations could be achieved, for example, by use of a bi-specific antibody having one variable region specific for an epitope present on the autoimmune antigen residing in the cleft of the MHCII receptor and, a second variable region specific for an epitope present on the $CD8^+$ receptor. The production of antibody specific for the polypeptide of the invention is a matter of routine to those of skill in the art, as is the preparation of bi-specific antibodies having specificity for 2 or more epitopes.

Polypeptide analogs of the present invention may be designed which will compete for recognition of self-antigens at the level of antigen presentation. Since MHC molecules contain a single peptide binding site, it is possible to design polypeptides which will bind with high affinity to disease-associated MHC molecules, but will not activate disease-causing T-helper cells. Such polypeptides act as antagonists for self-antigen recognition. Precedent for such an approach arises from observation that a mouse lysozyme polypeptide, itself non-immunogenic, can compete for MHC binding with an immunogenic polypeptide from hen-egg white lysozyme and thereby reduce T cell activation by that polypeptide (Adorini, et al., *Nature*, 334:623–625, 1988). Similarly, such a therapeutic approach for screening effective polypeptide analogs has been utilized in such autoimmune diseases as experimental autoimmune encephalomyelitis (EAE) (Wraith, et al., *Cell*. 59:248, 1989; Urban, et al., *Cell*, 59:257, 1989).

The single-letter symbols used to represent the amino acid residues in the polypeptides of the present invention are those symbols commonly used in the art. The term "analog" refers to any polypeptide having a substantially identical amino acid sequence to a polypeptide provided herein and in which one or more amino acids have been substituted with chemically similar amino acids. For example, one polar amino acid, such as glycine or serine, may be substituted for another polar amino acid; or one acidic amino acid, such as aspartic acid may be substituted for another acidic amino acid, such as glutamic acid; or a basic amino acid, such as lysine, arginine, or histidine may be substituted for another basic amino acid; or a non-polar amino acid such as alanine, leucine, or isoleucine may be substituted for another non-polar amino acid.

The term "analog" also means any polypeptide which has one or more amino acids deleted from or added to a polypeptide of the present invention, but which still retains a substantial amino acid sequence homology to such peptide. A substantial sequence homology is any homology greater than 50%. The term "fragment" means any shorter version of the polypeptides identified herein having at least 6 amino acid residues, wherein the fragment is capable of stimulating proliferation of islet infiltrating T lymphocytes (IITLs), or is a fragment capable of inhibiting the stimulation of such cells by a stimulating polypeptide fragment.

The term "chemical derivative" means any polypeptide derived from a polypeptide of the present invention and in which one or more amino acids have been chemically derivatized by reaction of the functional side groups of amino acid residues present in the polypeptide. Thus, a "chemical derivative" is a polypeptide that is derived from the sequences or polypeptides identified herein by one or more chemical steps. Such derivatized molecules include, for example, those molecules in which free amino groups have been derivatized to form amine hydrochlorides, P-toluene sulfoamides, benzoxycarboamides, T-butyloxycarboamides, thiourethane-type derivatives, trifluoroacetylamides, chloroaceamides, or formamides. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides which contain one or more naturally occurring amino acids derivatives of the 20 standard amino acids. For example, 4-hydroxyproline may be substituted for proline; 5-hydroxylysine may be substituted for lysine; 3-methylhistidine may be substituted for histidine; homoserine may be substituted for serine, and ornithine may be substituted for lysine.

It should be understood that the present invention is not limited to the illustrative polypeptides depicted in Table 1, instead, a polypeptide falling within the scope of this invention may extend outside of, or comprise less than, the region between amino acid 28 and amino acid 50 of coxsackie virus P2-C, or between amino acid 250 and amino acid 273 of $GAD_{65}$, or between amino acid 258 and amino acid 281 of $GAD_{67}$, as long as a substantial part of a given polypeptide is characterized by an amino acid sequence from that region, or segments or combinations thereof, and the polypeptide demonstrates the desired immunological or biological activity against autoimmune disease. In addition, polypeptides according to this invention include those having amino add sequences which are longer or shorter in length than those of the polypeptides illustrated in Table 1, or which comprise segments or combinations thereof, as long as such polypeptides consist substantially of the region between the amino adds illustrated in Table 1 and demonstrate immunological or biological activity. Furthermore, polypeptides according to this invention include those characterized by a sequence of amino acids which is longer or shorter than that of the GAD$_{65}$ polypeptide of Table 1, or which comprise segments of that polypeptide and which display immunological or biological activity against the autoimmune disease. All polypeptides of the invention should not stimulate or enhance the autoimmune disease.

Accordingly, it should be understood that the specific selection of any one polypeptide within the polypeptides of the invention does not involve undue experimentation. Such a selection may be carried out by taking a number of polypeptides and testing them for their immunological and biological activity in ameliorating the autoimmune disease. The NOD mouse represents an excellent and well characterized model for screening polypeptides of the invention capable of ameliorating diabetes.

The polypeptides according to the present invention may be prepared by recombinant techniques or by conventional synthesis using known polypeptide synthetic methods, including synthesis on a solid support. An example of a suitable solid phase synthetic technique is that described by Merriweather (J. Am. Chem. Soc., 85:2149, 1963). Other polypeptide synthetic techniques may be found, for example, in Bodanszky, et al., Peptide Synthesis, John Wiley & Sons, 2d ed., 1976, as well as other references known to those skilled in the art. A summary of polypeptide synthesis techniques can be found in Stewart, et al., Solid Phase Peptide Synthesis, Pierce Chemical Company, Inc., Rockford, Ill., 1984. The synthesis of polypeptides by solution methods may also be used, for example, as described in The Proteins, Vol. II, 3d ed., Neurath, et al., eds., 105, Academic Press, New York, N.Y., 1976. Appropriate protective groups for use in such synthesis can be found in the above references as well as in J. McOmie, Protective Groups in Organic Chemistry, Plenum Press, New York, N.Y., 1973.

The polypeptides of the invention may also be prepared in an appropriate host transformed with DNA sequences that code for the desired polypeptide. For example, a polypeptide may be prepared by the fermentation of appropriate hosts that have been transformed with and which express a DNA sequence encoding the polypeptide. Alternatively, a DNA sequence encoding several of the polypeptides of this invention may be linked together and those sequences may then be used to transform an appropriate host to permit the expression of polypeptides involved in the autoimmune disease.

The dosage ranges for the administration of the GAD$_{65}$ polypeptides of the invention are those large enough to produce the desired effect in which the symptoms or cellular destruction of the autoimmune response are ameliorated. The dosage should not be so large as to cause adverse side effects, such as unwanted cross-reactions, anaphylactic reactions, and the like. Generally, the dosage will vary with the age, condition, sex, and extent of the disease in the patient and can be determined by one of skill in the art. The dosage can be adjusted by the individual physician in the event of any counterindications. Dosage can vary from about 0.1mg/m$^2$ to about 2000 mg/m$^2$, preferably about 0.1 mg/m$^2$ to about 500mg/m$^2$/dose, in one or more dose administrations daily, for one or several days.

The GAD$_{65}$ polypeptides of the invention can be administered parenterally by injection or by gradual perfusion over time. The GAD$_{65}$ polypeptides of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the GAD$_{65}$ polypeptides of the invention, the medicament being used for therapy of autoimmune response to GAD$_{65}$.

The above disclosure generally describes the present invention. A more complete understanding can be obtained by reference to the following specific examples which are provided herein for purposes of illustration only and are not intended to limit the scope of the invention.

EXAMPLE 1

Cloning and Expression of GAD$_{65}$

A. RECOMBINANT DNA PROCEDURES

In order to obtain cDNA probes specific for GAD$_{65}$ and GAD$_{67}$, total RNA was extracted from adult rat brain by guanidine isothiocyanate-cesium gradient using the method of Chirgwin, et al. (Biochemistry, 18:5294, 1979). Poly (A) RNA was purified on oligo dT cellulose, using the protocol by Bethesda Research Laboratories (BRL). First strand synthesis was performed by using MMLV-reverse transcriptase (BRL), with conditions suggested, except that poly d(N$_6$)-mers (Pharmacia) were used as primers. This cDNA-RNA mixture was heat inactivated at 65° C. for 15 min and stored at −20° C. For PCR, 1/50 of the sample was added to the 100 µl reaction. Degenerate oligonucleotides were synthesized (Applied Biosystems) to encode the underlined common amino acid sequences of feline (from cDNA) (Kobayashi, et al., J. Neurosci., 7:2768, 1987) and rat (from peptides) (Chang and Gottlieb, J. Neurosci., 8:2123, 1988) GAD (FIG. 1). The 5'-end sequence of each degenerate oligonucleotide contained one strand of the DNA sequence recognized by either SstI and HindIII (5' oligo) or SstI and SstII (3'-end oligo). These primers were used for selective amplification by polymerase chain reaction of the generated cDNA template as described by Gould, et al. (Proc. Natl. Acad. Sci., USA, 86:1934, 1989). PCR products were subcloned into HindIII/SstI double digested Bluescript SK vector (Stratagene), transformed into DH5 (BRL), and plated by standard methods (Maniatis, et al., Molecular Cloning: A Laboratory Manual, Cold Spring Harbor Laboratory, Cold Spring Harbor, N.Y., 1989).

Colony hybridization was done with an 5'-$^{32}$P end labeled oligonucleotide specific to feline GAD$_{67}$ (Kobayashi, et al., J. Neurosci., 7:2768, 1987). End labeling of oligonucleotide, hybridization conditions, and washing conditions were done as described (Wallace, et al., in Guide to Molecular Cloning Techniques; Berger, et al., Eds. in Methods of Enzymology; Abelson, et al., Eds. Academic Press, Inc., San Diego, 432–442, 1987), except that the nitrocellulose filters were washed at 50° C. for 15 min. Colonies which were positive and negative in the hybridization were individually picked and grown overnight in Terrific Broth (Tartof, et al., Focus, 9:12, 1987). DNA was isolated using a boiling method (Maniatis, et al., *Molecular Cloning: A Laboratory Manual*, Cold Spring Harbor Laboratory, Cold Spring Harbor, N.Y., 1989) and templates were denatured by 0.2N NaOH and purified by Sephacryl S400 spun columns (Pharmacia). Sequencing of denatured double stranded template was by the chain-termination method (Sanger, et al., *Proc. Natl. Acad. Sci., USA*, 74:5463, 1977) using the T7-sequencing kit (Pharmacia).

As shown in FIG. 1, PCR-generated rat $GAD_{65}$ and $GAD_{67}$ cDNAs were used as probes to screen a lambda ZAP (Stratagene) rat hippocampus library provided by S. Heinemann (Salk Institute) by standard techniques (Maniatis, et al., *Molecular Cloning: A Laboratory Manual*, Cold Spring Harbor Laboratory, Cold Spring Harbor, N.Y., 1989). A 2400 nucleotide $GAD_{65}$ cDNA (the largest clone) was isolated and subcloned by "zapping" as described by Stratagene. When a rat GAD67 cDNA was obtained which was smaller than a 3.2 kb rat $GAD_{67}$ cDNA clone already on hand, the larger cDNA was sequenced. Exo III deletions (Henikoff, *Gene*, 28:351, 1984) were made in both directions for $GAD_{65}$ and $GAD_{67}$ and templates were prepared and sequenced as described above. Anchored PCR (Frohman, et al., *Proc. Natl. Acad. Sci., USA* 85:8998, 1988) was done to clone the remaining 5'-ends of $GAD_{65}$ and $GAD_{67}$ mRNAs which were not represented in the original cDNA clones isolated in the library screening. Sequencing of these clones revealed that neither $GAD_{65}$ nor $GAD_{67}$ mRNAs contained any further initiation codons (AUGs) in frame with the previously designated initiation codons of the original cDNA clones.

EXAMPLE 2

Characterization of Cloned $GAD_{65}$

A. NORTHERN BLOT HYBRIDIZATION

Two PCR-derived cDNA probes were hybridized to Northern blots containing rat brain RNA in order to determine whether the $GAD_{67}$ and $GAD_{65}$ cDNAs were derived from two different mRNAs. RNA was extracted as described in Example 1. Poly (A) RNA was separated by electrophoresis in formaldehyde and transferred onto Biotrans (ICN) membranes, and hybridization was performed as described by Well, et al. (*J. Neurosci.*, 16:311, 1986), except that 100 µl/ml of poly (A) was added. Probes were labeled to approximately $10^9$ dpm/µg by the oligolabeling procedure of Feinberg and Vogelstein (*Anal. Biochem.*, 132:6, 1983). Identical results were subsequently obtained with full-length clones of $GAD_{65}$ and $GAD_{67}$ cDNAs.

Figure 5:
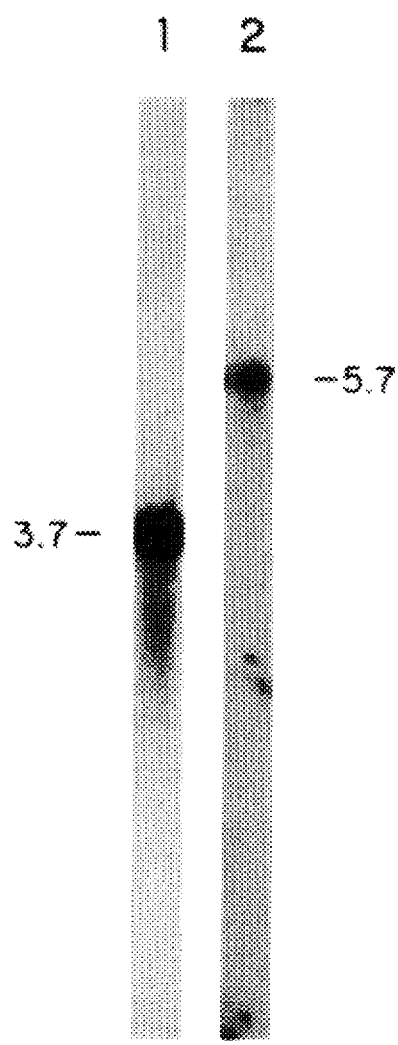
FIG. 5 GAD$_{65}$ and GAD$_{67}$ cDNAs hybridize to different size RNAs.

As shown in FIG. 5, lanes 1 and 2 contain 1 µg of poly (A) selected RNA extracted from rat cerebellum. Lane 1 was hybridized to a cDNA probe for the rat cognate of feline $GAD_{67}$ (Kobayashi, et al., *J. Neurosci.*, 7:2768, 1987) and lane 2 with a cDNA probe for the rat peptide sequence (which corresponds to $GAD_{65}$). The cDNA probe for the rat peptide sequence hybridized to a 5.7 kb RNA, while the cDNA probe for the rat cognate of our feline cDNA, hybridized to a 3.7 kb RNA. This demonstrates that $GAD_{65}$ and $GAD_{67}$ are not derived from the same mRNA.

B. GENOMIC HYBRIDIZATION OF $GAD_{67}$ AND $GAD_{65}$

In order to investigate the possibility that $GAD_{67}$ and $GAD_{65}$ arise from separate genes, cDNAs of both $GAD_{67}$ and $GAD_{65}$ were hybridized to DNA blots containing genomic DNA.

For Southern blots, genomic DNA was extracted from rat liver as described (Kaiser, et al., in *DNA Cloning*, vol. I, A Practical Approach, D. M. Glover ed., IRL Press, Oxford, 38–40, 1985). DNA (10 µg/sample) was digested to completion with EcoRI and HindIII using conditions recommended by the suppliers (BRL Gaithersburg, Md.). DNA fragments were separated by electrophoresis at 1.5 v/cm for 16 hrs in 0.8% agarose. The DNA was then transferred to Zeta-Probe membranes (Bio-Rad), hybridized, and washed, as described by Gatti, et al. (*Biotechniques*, 2:148, 1984), except that 5 µg/ml Carnation dried milk was substituted for Denhardt's solution. Probes for Southern blots were labeled as described in Example 1, above.

Figure 6:
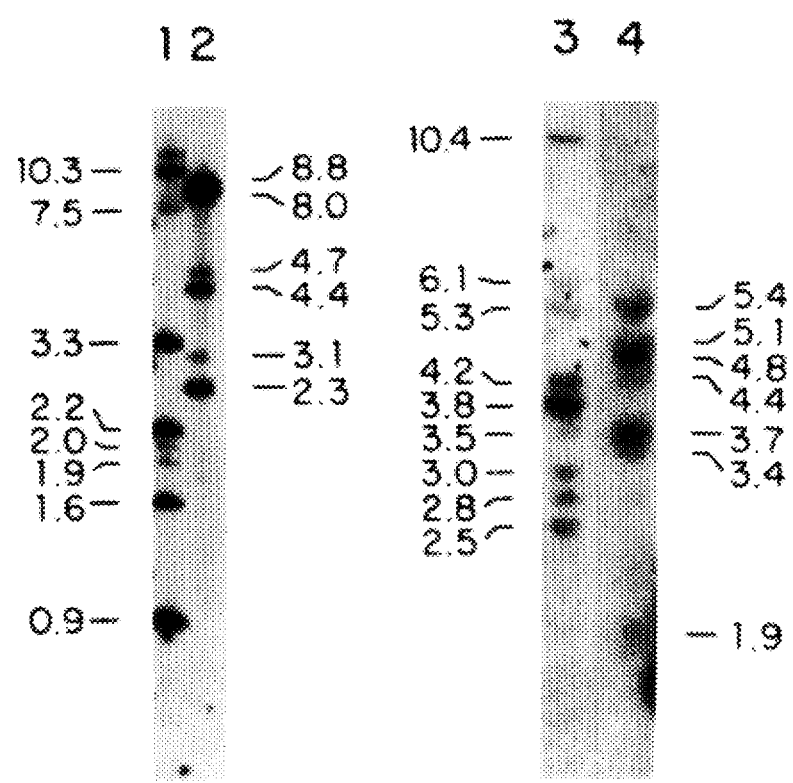
FIG. 6 Southern blots hybridized with cDNA probes specific for GAD$_{65}$ and GAD$_{67}$.

As shown in FIG. 6, genomic DNA digested with HindIII and EcoRI are in lanes 1 and 3 and lanes 2 and 4, respectively. $GAD_{67}$ cDNA was hybridized to lanes 1 and 2, whereas $GAD_{65}$ cDNA was hybridized to lanes 3 and 4. Numbers along the side of the gel are the DNA fragment sizes in kilobases.

This data shows that the two cDNAs hybridize to genomic fragments of different sizes. In addition, the greatest contiguous stretch of identical nucleotide sequence of $GAD_{65}$ and $GAD_{67}$ cDNAs is only 17 nucleotide bases in length. Thus, $GAD_{67}$ and $GAD_{65}$ are encoded by two distinct genes.

C. ENZYMATIC COMPARISON OF $GAD_{67}$ AND $GAD_{65}$

Studies were done comparing the effect of PLP on the activity of $GAD_{67}$ and $GAD_{65}$. In so doing, both cDNAs were subcloned into vectors that allowed their expression in bacteria (Studier, et al., *J. Mol. Biol.*, 189:113, 1986). Overexpression of "fusionless" $GAD_{65}$ and $GAD_{67}$ was accomplished by subcloning $GAD_{65}$ cDNA into the NcoI site of pET-8c and $GAD_{67}$ cDNA into the NheI site of pET-5c vectors (Studier, et al., *J. Mol. Biol*, 189:113, 1986).

To obtain compatible sticky ends for correct in-frame subcloning of both cDNAs, selective amplification was performed by PCR using conditions suggested by United States Biochemical (USB), with 200 µM dNTPs and 1.5 mM $MgCl_2$ in the mixture and annealing at 55° C. with 20 cycles to decrease infidelity of AmpliTAQ (USB). Primers specific for $GAD_{65}$ and $GAD_{67}$ contained one DNA strand of the NcoI and SpeI recognition sites, respectively. Since there is a NheI restriction site within the coding region of $GAD_{67}$, SpeI (which is compatible with NheI) was used.

PCR products were subcloned into their respective pET vectors, transformed into DH5 and plated as described (Maniatis, et al., *Molecular Cloning: A Laboratory Manual*, Cold Spring Harbor Laboratory, Cold Spring Harbor, N.Y., 1989). Colonies were picked and grown overnight in LB broth with 50 µg/ml ampicillin. Subclones with correct orientation were transformed into BL21 (DE3) strain (Studier, et al., *J. Mol. Biol.*, 189:113, 1986) for overexpression. As a negative control, the pET-8C vector with no insert was transformed and subsequently induced. Single colonies were picked, grown, induced by 1 mM isopropyl-B-D-thiogalacto-pyranoside (IPTG), and analyzed on SDS-PAGE gels as described (Sambrook, et al., *Molecular Cloning a Laboratory Manual*, Cold Spring Harbor Laboratory Press, Cold Spring Harbor, 17.15–17.16, 1989).

To measure GAD activity, we induced 10 ml cultures of bacteria at $OD_{600}$—0.5 with 1 mM IPTG. Two hours after induction, bacteria was spun down and resuspended and sonicated in 1 ml of homogenizing buffer (1 mM phenylmethylsulfonyl fluoride (PMSF), 1 mM 2-aminoethylisothiouronium bromide (AET), and 60 mM potassium phosphate, pH 7.1). After sonication, cell debris was removed by centrifugation and protein concentration was measured (Bradford, *Anal. Biochem.*, 72:248, 1986) in the supernatant (supernatant was stored in aliquots at −70° C.). Brain homogenates were prepared as described (Legay, et al., J. Neurochem., 46:1478, 1986). GAD activity was measured as described (Krieger, et al., J. Neurochem., 33:299, 1984) with 0.2 mM PLP present or absent and 20 µl of brain homogenate or bacterial lysate in the incubation mixture. Production of $^{14}CO_2$ in bacterial lysates was linear with respect to time of incubation and protein concentration.

TABLE 2

| Source | GAD Specific Activity* | | Fold Increase in Induction |
|---|---|---|---|
| | − PLP | + PLP | |
| BL21(DE3) + pET-8c | 12 ± 0.4 | 9 ± 1 | — |
| BL21(DE3) + pET-GAD$_{65}$ | 115 ± 3 | 773 ± 61 | 6.7 |
| BL21(DE3) + pET-GAD$_{57}$ | 160 ± 2 | 389 ± 8 | 2.4 |
| Rat Brain | 131 ± 5 | 216 ± 2 | 1.6 |

*cpms of $^{14}CO_2$/µg protein/hr of triplicates ± S.E.M.

As shown in Table 2, bacterial lysates containing GAD$_{65}$ or GAD$_{67}$ catalyze the conversion of [1-$^{14}$C]-glutamate to GABA and $^{14}CO_2$.

PLP stimulates the enzymatic activity of GAD$_{65}$ more than GAD$_{67}$. This greater stimulation probably reflects the faster cycling of GAD$_{65}$ through the inactivation cycle proposed by Martin and coworkers (Martin, Cell. Mol. Neurobiol., 7:237, 1987). This faster cycling suggests that GAD$_{65}$ contributes more to the pool of apo-GAD that exists in vivo (Miller, et al., Brain Res. Bull., 5(Suppl.2):89, 1980). Thus, in vivo, PLP appears to regulate GAD$_{65}$ activity more than GAD$_{67}$ activity.

GAD$_{65}$ activity in bacterial lysates is similar to the five-fold PLP stimulation of GAD activity found in synaptosomes prepared from rat substantia nigra (Miller, et al., J. Neurochem., 33:533, 1979). Because both GADs are more dependent upon added PLP in bacteria than is the GAD activity in crude rat brain homogenates, the endogenous PLP concentration of bacteria lysates may be less than rat brain homogenates.

D. IMMUNOLOGICAL IDENTIFICATION OF GAD$_{65}$ AND GAD$_{67}$

Rat brain homogenates and bacterial lysates were extracted as described above. Equal volumes of loading buffer were added to each sample as described (Harlow, et al., Antibodies, A Laboratory Manual, Cold Spring Harbor Laboratory, Cold Spring Harbor, N.Y., 1988). Proteins were separated by electrophoresis in a 10% acrylamide gel in SDS and electrophoretically transferred to nitrocellulose (Harlow, et al., Antibodies, A Laboratory Manual, Cold Spring Harbor Laboratory, Cold Spring Harbor, N.Y., 1988). The unreacted sites were blocked with a phosphate buffered saline (PBS) solution containing 2% bovine serum albumin (fraction V), 1% gelatin, and 1% Triton-X-100 at 42° C. for one hr. After washing, the nitrocellulose filter was then cut into three sections and incubated with the following primary antibodies: lanes 1 to 4 with a 1/2000 dilution of the antiserum of Oertel, et al. (Neuroscience, 6:2689, 1981 ), which recognizes both GAD$_{67}$ and GAD$_{65}$; lanes 5–8 with a 1/2000 dilution of K-2 antiserum, which recognizes only GAD$_{67}$; lanes 9–12 with a 1/2000 dilution of GAD-6 monoclonal antibody, which is specific for GAD$_{65}$ (Chang, et al., J. Neurosci., 8:2123, 1988). All filters were extensively washed and appropriate secondary antibodies were incubated and washed. Bound antibodies were detected with $^{125}$I-labeled protein A and autoradiography. Each lane contained the following: lanes 1, 5, and 9 are BL21 (DE3)+ pET-GAD$_{67}$; lanes 2, 6, and 10 are BL21(DE3)+pET-GAD$_{65}$; lanes 3, 7, and 11 are rat brain homogenate; and lanes 4, 8, and 12 are BL21 (DE3)+pET-8c.

Figure 7:
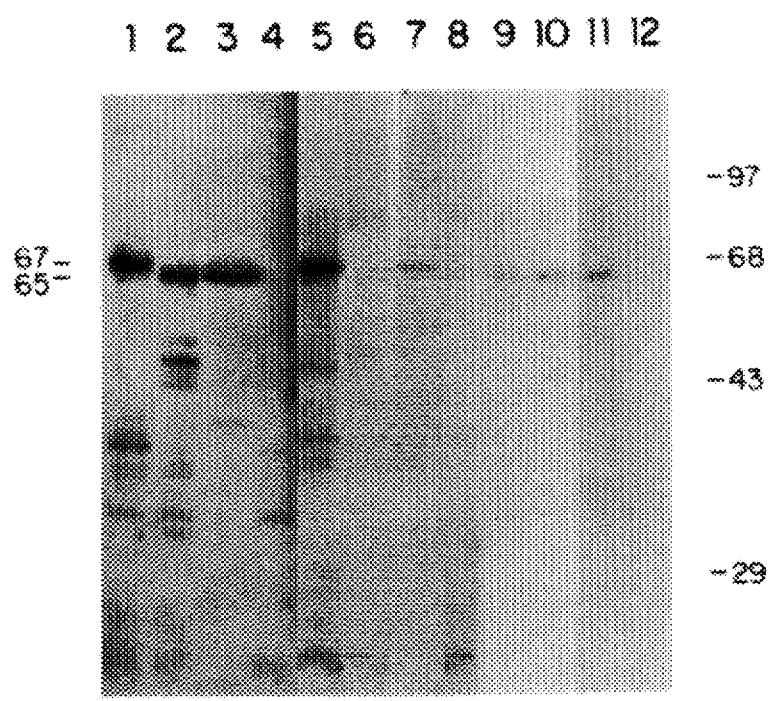
FIG. 7 Immunological identification of GAD$_{65}$ and GAD$_{67}$.

The immunoblots of bacterially produced GAD$_{65}$ and GAD$_{67}$ demonstrated that GAD$_{65}$ indeed corresponds to the smaller GAD in brain extracts, and GAD$_{67}$ to the larger form (FIG. 7). Previous work has demonstrated the correspondence of GAD$_{67}$ to the larger GAD for feline GAD$_{67}$, and for mouse GAD$_{67}$ (Katarova, et al., Eur. J. Neurosci., 2:190, 1990; 235, 1987). The mobilities of bacterially produced GAD$_{65}$ and GAD$_{67}$ (as detected with the antiserum of Oertel, et al. (Neuroscience, 6:2689, 1981) are identical to the immunoreactive doublet seen in rat brain homogenate.

The smaller molecular weight and larger molecular weight forms of GAD in rat brain are thus identical in antigenicity and size to the products of GAD$_{65}$ and GAD$_{67}$ cDNAs, respectively. Consequently, the two GADs in rat brain are GAD$_{65}$ and GAD$_{67}$. From this data it can also be concluded that the molecular identity of the reported PLP-dependent and PLP-independent GADs by Tapia (Bayon, et al., J. Neurochem., 29:519, 1977) am GAD$_{65}$ and GAD$_{67}$, respectively. Martin and coworkers (Spink, et al., Brain Res., 421:235, 1987) have reported the existence of four kinetically different forms of rat brain GAD. However, immunoblotting experiments (with the antisera used here) of these forms have not been reported.

E. DISTRIBUTION OF GAD$_{65}$ and GAD$_{67}$ IN RNAs IN BRAIN TISSUE

Experiments were done to determine the distribution of GAD$_{65}$ and GAD$_{67}$ in RNAs in cerebellum using in situ hybridization.

Transcripts of, respectively, 3.2 kb and 2.3 kb from GAD$_{65}$ and GAD$_{67}$ cDNAs, were radiolabeled with $^{35}$S according to Wuenschell, et al. (Proc. Natl. Acad. Sci., USA 83:6193, 1986) procedure. Hydrolyzed fragments of 200 bp were hybridized to coronal sections of a rat cerebellum. Animals were anesthetized under halothane and decapitated. The brain was rapidly frozen in dry ice and coronal frozen sections (12 µm) were fixed for 30 min in freshly prepared 4% formaldehyde in phosphate-buffered saline (PBS; 130 mM NaCl, 10 mM Na phosphate, pH 7.0.). The tissue was dehydrated through graded ethanol solutions and stored at −70° C.

In order to increase tissue permeability, the sections were submitted to the following pretreatments: rehydration through graded ethanol solutions (5 min each in 95%, 85%, 70%, 50%, and 30% ethanol); PBS (5 min); 0.02N HCl (10 min); PBS (5 min); 0.01% Triton N-101 in PBS (1 min); PBS (2×5 min); 1 µg/ml proteinase K (7.5 min); and glycine (to inhibit proteinase K) in PBS (3×5 min). Proteinase K was digested for 30 min at 37° C. before use. Sections were then incubated at 37° C. in 50% formamide, 750 mM NaCl, 25 mM EDTA, 0.2% SDS, 0.02% BSA, 0.002% Ficoll, 0.02% polyvinylpyrrolidone, 250 µg/ml yeast tRNA, 250 µg/ml poly A, and 25 mM PPES (pH 6.8).

For the hybridization, 100 mM DTT, 10% dextran sulfate, and sense or antisense $^{35}$S-RNA were added to the prehybridization solution. An aliquot (50 µl) of the hybridization solution containing about 3 ng ($10^6$ cpm) of probe (sense or antisense) was added onto the slides. Each slide was coverslipped and incubated for 16 hrs at 50° C., following which the siliconized coverslips were removed by brief washing in 4×SSC (1×SSC−150 mM NaCl, 60 mM Na citrate, pH 7.0).

Sections were then treated with ribonuclease A (50 µg/ml in 0.5M NaCl, 10 mM Na thiosulfate, 1 mM EDTA, 10 mM TrisHCL pH 8.0) for 20 min at 37° C. and rinsed for 2 hrs at room temperature in 2×SSC, 10 mM Na thiosulfate, for 30 min at 55° C. Sections were dehydrated in ethanol, delipidated in xylene, coated with Kodak NTB2 emulsion and exposed for 10 days at 4° C. The emulsion was developed with Kodak D19, and the tissue counterstained with cresyl violet.

Autoradiographic grains were detected using reflected polarized light and grain numbers, densities, nd cell areas were determined with an Analytic Imaging Concepts image analyzer system. Due to the low background level, the criteria for defining a cell "labeled" was based on the presence of more than 5 clustered grains. The GAD labeled cells were found scattered throughout the brain, enabling the measurement of the number of grains over individual cells. The boundary of the cell and the area covered by a grain allowed the calculation of the number of grains per cell. This analysis was done at a high magnification (800 X), using both reflected polarized light and transmitted light to simultaneously visualize the stained cell and the superimposed grins. Numbers are means ±S.E.M. of "n" cells.

TABLE 3

| CELL TYPE | GRAINS/CELL | | |
|---|---|---|---|
| | $GAD_{67}$mRNA | $GAD_{65}$mRNA | $GAD_{67}$:$GAD_{65}$ |
| Purkinje | 172 ± 34 (87)* | 43 ± 2 (70) | 4.0 |
| Golgi II | 96 ± 8 (80) | 64 ± 9 (65) | 1.5 |
| Basket | 61 ± 12 (102) | 16 ± 1 (57) | 3.8 |
| Stellate | 55 ± 15 (65) | 18 ± 3 (37) | 3.1 |

*± S.E.M.(n)

In all neuronal types $GAD_{67}$ mRNA levels are greater. The observations with in-situ hybridization are consistent with previous findings (Nitsch, *J. Neurochem.*, 34:822, 1980; Denner, et al., *J. Neurochem.*, 44:957, 1985; Itoh, et al., *Neurochem. Res.* 15 6:1283, 1981) that the ratio of PLP dependent to independent GAD activities in the cerebellum is one of the lowest in brain regions tested. In addition, as shown in Table 3, the order of amounts for $GAD_{67}$ mRNA is Purkinje>Golgi II>Basket>Stellate cells; in contrast, for $GAD_{65}$ mRNA, this order is Golgi II>Purkinje>Basket>Stellate cells.

The expression of $GAD_{65}$ and GAD67 mRNAs thus differs among classes of neurons. The contribution of each to total GAD activity in turn affects how GABA production is regulated. For example, the substantia nigra contains one of the highest ratios of PLP-dependent to PLP-independent GAD activities (Nitsch, *J. Neurochem.*, 34:822, 1980). Increasing GABA concentration in the substantia nigra by local injection of inhibitors of GABA catabolism is especially effective in reducing seizure susceptibility (Gale, *Fed. Proc.*, 44:2414, 1985). Experimental animals undergoing seizures induced by PLP-antagonists may therefore be unable to inhibit seizure propagation because of inhibition of $GAD_{65}$ particularly in nerve terminals within the substantia nigra.

F. SUBCELLULAR LOCATION OF $GAD_{65}$ AND $GAD_{67}$

The distribution of $GAD_{65}$ and $GAD_{67}$ was evaluated in the $S_2$ and synaptosome subcellular fractions. $S_2$ is a high speed supernatant consisting of the cytosol of all cells in the brain, while the synaptosomal fraction consists primarily of nerve endings (Gray, et al., *J. Anat., Lond,* 96:79, 1962). For these studies, whole rat brain fractionation was performed as described by Booth and Clark (Booth, et al., *Biochem. J.,* 176:365, 1978). Protein concentrations were determined by Schaffner and Weissman (Schaffner, et al., *Anal Biochem.* 56:502, 1973). Samples were prepared as described (Kaiser, et al., *DNA Cloning, Vol. I, A Practical Approach, D. M. Glover ed.* (IRL Press, Oxford, 1985, pp. 38–40), and immunoblotting was done as described above using GAD-6 monoclonal antibody and K-2 antiserum. Equal amounts of protein (16 µg) were added to each lane. Autoradiography showed a linear response of increasing amount of $^{125}$I-protein A bound to antibody with protein concentrations of 1, 3, 10, 30, 100 µgs with both K-2 antiserum and GAD-6 monoclonal antibody (data not shown).

The results showed that GAD67 was present in equal amounts in both fractions. Since the $S_2$ fraction contains the cytosolic proteins of glial (as well as other non-neuronal) and neuronal cells, the concentration of GAD67 must be greater in neuronal cell bodies than in nerve endings. In contrast, the concentration of $GAD_{65}$ was greater in synaptosomes than in $S_2$. These subcellular fractionation experiments suggest that, in contrast to $GAD_{65}$, a much greater fraction of $GAD_{67}$ is present in cell bodies of neurons than in nerve terminals. Thus, subcellular fractionation, like immunohistochemistry, shows that $GAD_{65}$ and $GAD_{67}$ have different subcellular distributions.

In vivo experiments utilizing inhibitors of GABA synthesis and degradation have suggested that the GABA pool in neuronal cell bodies is different from that in the nerve terminals (Iadarola, et al., *Mol. Cell. Biochem.*, 39:305, 1981). GABA produced by $GAD_{67}$ may be involved more in cellular metabolism (for example, in the GABA shunt) and in dendrodandritic synapses. The dendrites of granule cells in the olfactory bulb, which form dendrodendritic synapses with mitral dendrites (Shepard, *Physiol Rev.*, 52:864, 1972) and probably release GABA (McLennan, *Brain Res.*, 29:177-184, 1971), label intensely with K-2 antiserum. While not shown here, it has also been found greater $GAD_{67}$ than $GAD_{65}$ mRNA levels (2-3 fold) in the olfactory bulb. This distribution is consistent with the reported finding that most GAD activity in the olfactory bulb is present in $S_2$ and $P_1$ (crude nuclear pellet) and not in synaptosomes (Quinn, et al., *J. Neurochem.*, 35:583, 1980).

The differing subcellular distributions of $GAD_{65}$ and $GAD_{67}$ could result from cytoskeletal anchoring or from some unknown protein targeting mechanism. Some cytoskeletal proteins have distributions that resemble $GAD_{65}$ and $GAD_{67}$. For example, in cultured sympathetic neurons Peng, et al. (*J Cell. Biol.,* 102:252, 1986), demonstrate that 84% of tau is in axons while 100% of MAP-2 is in cell bodies and dendrites. In addition, 43 kd protein, a cytoskeletal protein, is thought to anchor the acetylcholine receptor to the underlying membrane cytoskeleton (Flucher, et al., *Neuron,* 3:163, 1989).

EXAMPLE 3

Detection of GAD Autoantibodies in Clinical Specimens

A. MATERIALS AND METHODS

1. Patient Specimens. Sera from four groups of individuals were selected from a previous study by Atkinson and co-workers (Atkinson, et al., *Lancet,* 335:1357–1360, 1990). These groups consisted of: Group (1), 1 new onset IDD patients diagnosed according to the established National Diabetes Data Group (NDDG) criteria (Gleichman, et al., *Diabetes,* 36:578–584, 1987) that had been referred to the University of Florida, Diabetes Clinics; Group (2), 5 randomly selected islet cell cytoplasmic antibody (ICA) negative non-diabetic controls without any known family history of autoimmune disease; Group (3), 13 individuals whose sera had been collected 3 to 66 months prior to their documented clinical onsets of IDD; Group (4), non-diabetic controls and relatives, and those who were studied prior to their onsets of IDD; and Group (5), 3 patients at risk for IDDM, but where onset has not yet occurred. This latter group had been ascertained through ongoing prospective ICA screening studies of more than 5000 first degree relative of IDD probands, and 8200 individuals from the general population (of which 4813 were school children).

2. Islet Cell Autoantibodies. ICA were assayed by indirect immunofluorescence on blood group O cryocut pancreatic (Atkinson, et al., *Lancet*, 335:1357–1360, 1990). All results were interpreted on coded samples, with control negative and positive sera in each batch. The degrees of ICA positivity were analyzed with the guidelines established by the Immunology Diabetes Workshop (IDW) for the standardization of ICA (Gleichman, et al., *Diabetes*, 36:578–584, 1987). All positive sera were titered by end point dilution, and the Juvenile Diabetes Foundation (JDF) units were determined by reference to a standard serum previously calibrated to the international JDF standard of 80 units. In the studies reported here, a positive ICA result was defined by replicate titers of 10 JDF units or greater.

3. HLA DR Typing. HLA DR typing was performed as adapted from the method described by Van Rood and Van Leuwen (*Nature*, 262:795–797, 1976), using DR trays (One Lamda Laboratories, Los Angeles, Calif.).

4. Human Islet Cells. Human pancreatic islets were isolated from cadaveric pancreases and maintained in vitro as previously described (Ricordi, et al., *Diabetes*, 37:413–420, 1988). The islet cells were metabolically labeled with $^{35}S$ methionine (Amersham, Arlington Heights, Ill.) in vitro (95% air/5%$CO_2$).

5. Islet Cell Extractions and Immunoprecipitations. Islet cells were extracted as previously described by Atkinson, et al. (*Lancet*, 335:1357–1360, 1990) with the following modifications. For immunoprecipitation studies, the islet cell lysates were precleared twice by incubation (2 h, 4° C.) with either control. IDD serum (100 µl), or GAD-6 (Chang, et al., *J. Neuro*, 8:2123–2130, 1988) (1 in 99 µl of Tris buffer (Atkinson, et al., *Lancet*, 335:1357–1360, 1990) for every 1000 islets. Immune complexes were then absorbed (1 h 4° C.) with an excess of protein A Sepharose CL-4B (Pharmacia, N.J.). Aliquot volumes representing 1000 islet cells containing unbound (precleared) lysate were then incubated (12 h, 4° C.) with either IDD or control sera (25 µl), or GAD-6 (Chang, et al., *J. Neuro*, 8:2123–2130, 1988) (1 µl in 25 µl Tris buffer). Following another incubation with protein A Sepharose CL-4B (1 h, 4° C.), the complexes were then washed 5 times with 50 mM Tris HCL (pH 7.4) with 0.1% SDS, 1.0% Triton X-114, and 2 mM EDTA, and then washed again one time in double distilled water. The protein A Sepharose CL-4B was then boiled in Laemmli sample buffer (Laemmli, *Nature*, 227:680–685, 1970), and the samples were subjected to SDS-PAGE and fluororadiography (Kodak, X-omat AR5) using Enhance (New England Nuclear). Alternatively, the autoradiographs were analyzed by a BETAGEN (Boston, Mass.) analyzer. Both 64 KA positive and negative sera were used in each assay, to serve as interassay controls. All fluororadiographs were analyzed and rated as positive or negative after comparison with the known interassay controls. Positive serum samples were designated as 1 when a sample resulted in immunoprecipitation of a low intensity 64,000 $M_r$ band, 2 if a moderate intensity band was observed and 3 if the intensity of the immunoprecipitated protein was high. A similar rating procedure was employed for the intensity of bands corresponding to immunoprecipitated $^{35}S$-$GAD_{65}$ and $^{35}S$-$GAD_{67}$.

6. Immunoprecipitations. Immunoprecipitation of bacterial lysates containing $^{35}S$-$GAD_{65}$ or $^{35}S$-$GAD_{67}$, and GAD from human brain homogenate, was completed as described above in immunoprecipitation studies of human islet cell extractions.

7. GAD Assays. Human brain homogenates were incubated with patient sera as described above in human islet cells. After absorption and washes, the protein A agarose slurry was aliquoted into three equal volumes and GAD activity was measured as described (Krieger, et al., *Neurochem.* 33:299, 1984). Briefly, Protein A agarose beads were incubated with (1-$^{14}C$)-glutamate (Amersham) in a designated incubation mixture (Krieger, et al., *Neurochem.* 33:299, 1984) and production of $^{14}CO_2$ was quantitated by a liquid scintillation counter.

8. Production of $^{35}S$-$GAD_{65}$ and $^{35}S$-$GAD_{67}$. Rat $GAD_{65}$ and $GAD_{67}$ cDNAs were subcloned into a bacterial expression system as previously described. Labeling of $^{35}S$-GADs was completed by pulsing IPTG induced bacterium (growing in Minimal Media) for 15 minutes with TRAN $^{35}S$-label (ICN). Cultures were then spun down and resuspended and sonicated in 1 ml of homogenizing buffer (1 mM phenylmethylsulfonyl fluoride (PMSF), 1 mM 2-aminoethylisothiouronium Bromide (AET) and 60 mM potassium phosphate, pH 7.1). After sonication, cell debris was removed by centrifugation and protein concentration was measured (Bradford, *Anal. Biochem.*, 72:248, 1986) in the supernatant (supernatant was stored in aliquots at −70° C.).

B. IMMUNOREACTIVITY OF IDDM SPECIMENS

Sera from patients with IDDM were tested for the ability to precipitate GAD from human brain homogenates.

TABLE 4

SERA FROM IDDM PATIENTS IMMUNOPRECIPITATE GAD ACTIVITY

| Patient | IDDM | Pre-IDDM Period[1] | 64K[2] | JDF[3] | GAD Activity[4] cpm's |
|---------|------|--------------------|--------|--------|-----------------------|
| DA | *5 | >24 | 3 | 164 | 13,762 |
| DC | * | >1 | 3 | 20 | 1,719 |
| RS | + | 5 | 3 | 40 | 588 |
| NL | + | 0 | 2 | 80 | 440 |
| DM | * | >1 | 2 | 10 | 184 |
| C | − | na | 0 | 0 | 280 |
| C | − | na | 0 | 0 | 285 |
| C | − | na | 0 | 0 | 325 |
| C | − | na | 0 | 0 | 275 |
| C | − | na | 0 | 0 | 270 |

[1]Expressed as months
[2]64K titers as described in Experimental Methods
[3]The islet cell antibody test as expressed in Juvenile Diabetes Foundation (JDF) units
[4]Not adjusted for background
[5]At risk for diabetes (also, failed glucose test)
na - Not applicable As shown in Table 4, the sera of four (out of five) at risk for IDDM or IDDM patients bound significantly greater amounts of enzymatically active GAD of human brain extracts than sera from control patients. In addition, sera from one of the patients was drawn in a pre-IDDM period, thus autoantibodies to GAD are present prior to the onset of IDDM symptoms (see C below).

Further experiments (results not presented) showed that the sera of two at risk IDDM patients (DA, DC) immunoprecipitated recombinantly produced $^{35}S$-$GAD_{65}$ whereas recombinantly produced $^{35}S$-$GAD_{67}$ was only recognized by sera of patient DA (and to a lesser degree than $^{35}S$-$GAD_{65}$). Subsequent studies have found larger titers of $GAD_{67}$ autoantibodies than $GAD_{65}$ are present in sera of IDDM patients with neuropathic complications (not shown here).

Additional studies using patient DA sera showed the presence of antibodies which recognize specific polypeptides produced in human pancreatic islet cells. Electrophoretic analysis of the bound polypeptides demonstrated the presence of autoantibodies to a 64 kD component, as previously shown by others in human IDDM (Baekkeskov, et al., *Nature*, 298:167–169, 1982) and in animal models (Baekkeskov, et al., *Science*, 224:1348–1350, 1984; Atkinson, et al., *Diabetes*, 37:1587–1590, 1988). Prior absorption of these sera with GAD-6 monoclonal, which recognized GAD65 but not $GAD_{67}$, or with bacterially produced $GAD_{65}$, abolished the ability of the sera to recognize the 64 kD pancreatic polypeptide. The epitopes recognized by autoantibodies to the 64 kD autoantigen are thus present in $GAD_{65}$, indicating that the autoantigen is indeed $GAD_{65}$. In order to investigate the predictive value of $GAD_{65}$, sera drawn from patients prior to onset of clinical manifestation of IDDM were tested for autoantibodies to $GAD_{65}$.

insulin therapy is needed. The sensitivity of such immunoassays will improve with the use of a recombinant $GAD_{65}$ of human origin which represents the GAD form present in β-cells of the pancreas.

EXAMPLE 4

Immune Proliferative Response to Polypeptide

Polypeptides were synthesized using an automatic instrument (Applied Biosystems) and standard conditions. These polypeptides were then tested to compare their relative ability to stimulate proliferation of splenic lymphocytes and islet infiltrating T lymphocytes (IITLs). In this study, polypeptides derived from the $GAD_{65}$ core sequence and from the homologous region of polio virus were compared. Appropriate cells were cultured for 5 days with the respective polypeptide in the presence of $5 \times 10^4$ irradiated spleen

TABLE 5

IDDM PATIENTS ANALYZED FOR AUTOANTIBODIES PRIOR TO THE ONSET OF DISEASE

| Patient | Sex | HLA | Age Onset[1] | Pre-IDD Period[2] | JDF | 64KA[3] | $GAD^3_{65}$ | $GAD^3_{67}$ |
|---|---|---|---|---|---|---|---|---|
| TA | M | 3,2 | 17 | 11 | 20 | 2 | 0 | 1 |
| CA | F | 4,5 | 38 | 4 | 0 | 1 | 1 | 0 |
| RA | M | 2,1 | 5 | 34 | 0 | 2 | 1 | 0 |
| TB | M | 2,4 | 11 | 66 | 40 | 1 | 1 | 0 |
| AB | M | N.D. | 23 | 6 | 160 | 3 | 3 | 2 |
| VC | F | 4,6 | 15 | 3 | 40 | 1 | 0 | 1 |
| JD | M | 6,1 | 34 | 25 | 10 | 3 | 1 | 1 |
| DR | F | 3,4 | 14 | 42 | 320 | 2 | 1 | 0 |
| JG | M | 3,3 | 12 | 8 | 40 | 1 | 0 | 0 |
| BR | M | 3,3 | 5 | 9 | 0 | 0 | 1 | 1 |
| KR | F | 4,X | 34 | 14 | 10 | 3 | 2 | 0 |
| JT | F | 4,6 | 7 | 10 | N.D. | 1 | 1 | 1 |

[1] Age of IDDM onset expressed as months
[2] The time interval between sera drawn and IDDM onset expressed as months
[3] 1 = lowest; 2 = medium; and 3 = highest band intensities
N.D. — not determined As shown in Table 5, 9 out of 12 specimens (75%) were immunoreactive with $^{35}$S-$GAD_{65}$. In addition, two patients (JA and VC) were immunoreactive to $GAD_{67}$, but not $GAD_{65}$ under these conditions. Therefore, in combination, autoantibodies to $GAD_{65}$ and $GAD_{67}$, were present in 11 out of 12 (91%) of these patients sera. This finding suggests that although autoantibodies to $GAD_{65}$ are more common than autoantibodies to $GADS_{67}$, the use of both recombinant GADs ($GAD_{65}$ and $GAD_{67}$) in an assay would allow for greater predictability of IDDM. Previous tests of these sera (Atkinson, et al., *Langet*, 335:1357–1360, 1990) demonstrated that 11 out of 12, or 92%, immunoreacted with the $^{35}$S-64 kD molecule from human pancreatic islet cells. The serum which contained detectable autoantibodies to the 64 kD molecule and not $GAD_{65}$ was a serum which contained the lowest titer (or "1") for the 64 kD molecule. Thus, the false negative obtained was due to a lack of sensitivity in this assay. Furthermore, this assay predicted IDDM in one patient (BR) who was negative for 64K.

These results show that the 64 kD molecule identified in β-cells of human pancreas is identical in size and antigenicity to rat $GAD_{65}$. Furthermore, sera drawn from patients prior to IDDM onset contain autoantibodies to $GAD_{65}$. Consequently, the $GAD_{65}$ recombinant molecule is of great utility as a diagnostic tool for predicting IDDM. The ability of a physician to diagnose IDDM prior to actual symptoms will no doubt result in a greater extension of time before cells. $^3$H-thymidine was added during the last 16 hours of culture.

TABLE 6

| ANTIGEN | AMINO ACID SEQUENCE | $^3$H-THYMIDINE INCORPORATION (cpm) BY LYMPHOID CELL POPULATION | |
|---|---|---|---|
| | | IITLs[a] | SPLEEN[b] |
| None | — | 1,100 | 6,500 |
| Poliovirus (SEQ ID NO. 04) | MKSMCPQAQLKCKYL | 900 | 22,500 |
| $GAD_{65}$ (SEQ ID NO. 05) | ARFKMFPEVKEKGMAA | 9,500 | 23,300 |

[a] islet infiltrating T lymphocytes ($3 \times 10^4$ cells/well)
[b] $1 \times 10^5$ cells/well In these studies, there was no significant difference in the proliferative activity of cultures of spleen lymphocytes exposed to either the polio or the $GAD_{65}$ polypeptides. However, both polypeptides stimulated a T cell response which was higher than that found in the media control. The lack of difference in proliferation in the spleen cell population may be due to a lower frequency of GAD polypeptide specific T cells.

The IITL population, when evaluated in the same manner, showed a marked difference in cell proliferation. In this system, the response to the GAD$_{65}$ polypeptide was 9-fold greater than that of either the culture media or the polio polypeptide. This data strongly suggests that the GAD$_{65}$ is an important antigen for T cell responses in the IITL population. This data suggests that molecular mimicry plays a role in the pathogenesis of diabetes.

The invention now being fully described, it will be apparent to one of ordinary skill in the art that many changes and modifications can be made without departing from the spirit or scope of the invention.

We claim:

1. An isolated polynucleotide sequence encoding the polypeptide of the amino acid sequence:

X-Pro-Glu-Val-Lys-Y-Lys-Z wherein X is an amino acid sequence selected from one to ten amino acids or omitted; Y is Glu; and Z is an amino acid sequence selected from one to eight amino acids or omitted wherein the polypeptide stimulates in vitro proliferation of human T lymphocytes.

2. The polynucleotide of claim 1 which is DNA.

3. The polynucleotide of claim 2 which is cDNA.

4. A polynucleotide according to claim 1, wherein X comprises Lys, Y is Glu and Z comprises Leu.

5. The polynucleotide according to claim 4, wherein X further comprises Met and Z further comprises Arg and Leu.

6. The polynucleotide according to claim 1, wherein X is the amino acid sequence Ala-Met-Met-Ile-Ala-Arg-Phe-Lys-Met-Phe and Z is the amino acid sequence Gly-Met-Ala-Ala-Leu-Pro-Arg-Leu.

* * * * *